US005783394A

United States Patent [19]

Bestwick et al.

[11] Patent Number: 5,783,394

[45] Date of Patent: Jul. 21, 1998

[54] RASPBERRY PROMOTERS FOR EXPRESSION OF TRANSGENES IN PLANTS

[75] Inventors: Richard K. Bestwick; Jill Anne Kellogg, both of Portland, Oreg.

[73] Assignee: Agritope, Inc., Beaverton, Oreg.

[21] Appl. No.: 788,928

[22] Filed: Jan. 24, 1997

Related U.S. Application Data

[63] Continuation-in-part of Ser. No. 592,936, Jan. 29, 1996.

[51] Int. Cl.[6] ..... C12Q 1/68; C12N 15/29; C12N 5/04; C07H 21/04

[52] U.S. Cl. ..... 435/6; 435/320.1; 435/419; 536/23.1; 536/24.3

[58] Field of Search ..... 435/6, 320.1, 419; 536/23.1, 24.3

[56] References Cited

FOREIGN PATENT DOCUMENTS

WO 95/35387 12/1995 WIPO ..... C12N 15/82

*Primary Examiner*—Nancy Degen
*Assistant Examiner*—William Sandals
*Attorney, Agent, or Firm*—Susan T. Evans

[57] ABSTRACT

The present invention is directed to the identification and isolation of two different promoter regions from the raspberry genome. The promoter regions are operably linked, in a native raspberry genome, to the coding region of a raspberry dru1 gene. Promoters of the invention are capable of regulating moderate level, constitutive expression of heterologous plant genes under their control. The invention is further directed to chimeric genes, cassette vectors, kits, transgenic plants, and methods employing such promoters.

34 Claims, 17 Drawing Sheets

Nsi I
dru1 pro
dru 1
Nsi I
Nsi I
dru1 pro
pAG-310 (5.8kb)
Nsi I
Eco RV
Xba I
Sna BI
GFP
dru1 pro
Sac I
Hind III
pAG-155 (5kb)
pAn
Eco RI
dru110 pro
Hind III
nptII
Bam HI
pAG-421

```
>Nsi_I
        10         20         30         40         50         60         70         80
ATGCATATCA ACAACTACGA ATAAAGAGAT CAGCCTTTCC GTATCTGGTG GATGTTTGAG TCGGTGATGA CCATCTAATT
        90        100        110        120        130        140        150        160
AAAGAAAGAA GAAAAATTAT ACATATTGTG GACCTCCCCA TATATAATTC TTATCATCTT TGTTACTGCC ATTATGATTA
       170        180        190        200        210        220        230        240
TAAAATGATA TTAAAGGGAT GGTGTACCGT GTACTAATCA AATATCTACC TGATCTTATT GATTTGAAAG ATCATAAAAA
       250        260        270        280        290        300        310        320
GAAATTAAAA TTGTTCAAAA TAAACCCCTA GAATTATATA TAGTTCATTA AGTTCAAATT AATTCGTTTG AAACGTGTTA
       330        340        350        360        370        380        390        400
AGCAACCCTA CAACGTACTA AGCACCCTAG CTCCCTTTGC CTCTCGGCGG TAAGAGGAGA TATCCTCAGT CGAATTATGA
       410        420        430        440        450        460        470        480
GCCGATCGAG GAAAGCTCGA TCAGTTGGAA AATCTTTCTT TCTTATGGCC AAGTTGTTTC AAACAATATA TTGAATTATT
       490        500        510        520        530        540        550        560
GACTCTTAGC AACTTAAGTT TCAAACCGTG ACGAACCAAT AAAATTTGAC AAATTAATCA CTTTAAGTGC CTAGTGGATC
       570        580        590        600        610        620        630        640
AGCGTCTAGG TTGGGAACCC CTCTACCTGC GTTTGATTCA CCAAGCTATC AAAATGGTCA GACACTGTGC TGCAATGCAC
       650        660        670        680        690        700        710        720
AATTGGAGCA TTTCACATGC GTTGCATGAA TTATTCCTTG GGTTAGGAAA CCTTTGAAAT ACCTTGACTA AGGTAAAAAA
       730        740        750        760        770        780        790        800
AAAAACTTGA CAAATTAATA AATATTAATA TTGATTTTGT ACGTACACGA CTTAACCAAA CTCTCAATGA TTTATTGATT
       810        820        830        840        850        860        870        880
TCTAATATAT ATATTAATAA NGTANGTCTA ATTGGATCAT TCATGATCTA CAGCCATCAC ATCTCAGATG ATTTTCTTGC
       890        900        910        920        930        940        950        960
AATGAATTGC CTAAGCTGGC GTTATTATCT TTTTTTCATA ATACAGTTTT AAAAAAGGGT ACGTATTGGA GCTGGTGATG
       970        980        990       1000       1010       1020       1030       1040
ACTTCTTAAG AAACAACAAA TTAACGCCAT AGCTATTTGA TTTATATATC CAAAAGGAGA AAATGTATAA GATCGTTGCT
                                                     >CAAT_box
      1050       1060       1070       1080       1090    |  1100       1110       1120
TACTTAATTT GCAGGCTAGG TTAATTGACA TCAAATAATT GAAGAGTACG TAGGGCCAAT GTTGCTGAGA TCTAGCATCA
      1130       1140       1150       1160       1170       1180       1190       1200
ATAATAGGAT TTGGCTTGTC GATCGATCAT CTTTATTTAA TTGAGAGGTA TGTATCCATA TGTTTTCTGA AATTAAAATA
                                                            >TATA_box
      1210       1220       1230       1240       1250       1260       1270       1280
TTACCTAATA ATTGAGCTGA AACTGTAGTG AATTTAACCT TTTCTAAGTT CTGCCCATAT ATAACATACC ACATAGGTAG
             >TATA_box                                                  >Start_codon
      1290   |   1300       1310       1320       1330       1340       1350       |
CTGATCGATC GATCATATAT ATGTACTTAG GGTTCTGATC AGTATCAATA TCGATCACAA GTGCTGATAA TTAAAC ATG
                                                                                   Met>
```

Fig. 6A

```
                                                                                  ___>
1360      1370       1380        1390       1400       1410       1420
GTT CTT CAA GGT AAG GTG GAG GCT GAC ATT GAA ATC TCA GCA CCT GCT GAC AAG TTC TAC AAC CTC
Val Leu Gln Gly Lys Val Glu Ala Asp Ile Glu Ile Ser Ala Pro Ala Asp Lys Phe Tyr Asn Leu>
___a___a___a___a___a___a___a___a___a__DRU1 EXONI___a___a___a___a___a___a___a___a___a___>

 1430      1440       1450       1460       1470       1480       1490
TTC AAG AGT GAG GCT CAC CAC GTC CCC AAA ACT TCT CAA ACT GGC ACC ATA ACC GGA GTT GCG GTG
Phe Lys Ser Glu Ala His His Val Pro Lys Thr Ser Gln Thr Gly Thr Ile Thr Gly Val Ala Val>
___a___a___a___a___a___a___a___a___a__DRU1 EXONI___a___a___a___a___a___a___a___a___a___>

    1500       1510       1520       1530       1540       1550
CAT GAA GGA GAC TGG GAA ACT GAT GGC TCC ATT AAG ATT TGG AAT TAT GCA ATA G GTAA
His Glu Gly Asp Trp Glu Thr Asp Gly Ser Ile Lys Ile Trp Asn Tyr Ala Ile Glu>
___a___a___a___a___a___a___a___DRU1 EXONI__a___a___a___a___a___a___a___a_>
                                                                        ____>

    1560       1570       1580       1590       1600       1610       1620       1630
GCCATTATGT TGTTAGATTG TTAATTTAGA TTATTAACCA AAGCTGGCTT TGAATCACTA CAATATATAT TAGGGCACGC
__________c__________c__________c_______INTRON I_______c__________c__________c__________>

    1640       1650       1660       1670       1680       1690       1700
CAGTACAGAT TTTCTGTTTA TAATTGTTTC AGTGATTATT TTCTTACAAA TATAG AG GGC GAA GTG GGA ACA TTC
                                                               Gly Glu Val Gly Thr Phe>
                                                             __b___DRU1 EXON II____b___>
__________c__________c___INTRON I__________c__________c_____>

 1710      1720       1730       1740       1750       1760       1770
AAG GAG AAA GTA GAG CTA GAC GAT GTG AAC AAG GCA ATA ATT CTG AAT GGG TTG GAA GGA GAT GTG
Lys Glu Lys Val Glu Leu Asp Asp Val Asn Lys Ala Ile Ile Leu Asn Gly Leu Glu Gly Asp Val>
___b___b___b___b___b___b___b___b___b_DRU1 EXON II__b___b___b___b___b___b___b___b___b___>

    1780       1790       1800       1810       1820       1830
TTC CAG TAT TAC AAG AGC TTC AAG CCC GTC TAT CAA TTC ACT CAA AAG AAT GAT GGC AGC AGC ATT
Phe Gln Tyr Tyr Lys Ser Phe Lys Pro Val Tyr Gln Phe Thr Gln Lys Asn Asp Gly Ser Ser Ile>
___b___b___b___b___b___b___b___b___b_DRU1 EXON II__b___b___b___b___b___b___b___b___b___>

1840       1850       1860       1870       1880       1890       1900
GCC AAA GTG TCC ATT GAA TAT GAG AAA CTG AGT GAG GAA GTT GCA GAT CCA AAT AAG TAC ATT CGC
Ala Lys Val Ser Ile Glu Tyr Glu Lys Leu Ser Glu Glu Val Ala Asp Pro Asn Lys Tyr Ile Arg>
___b___b___b___b___b___b___b___b___b_DRU1 EXON II__b___b___b___b___b___b___b___b___b___>

    1910       1920       1930       1940       1950       1960       1970
TTG ATG ACT AAT ATC GTC AAG GAT CTT GAT GCC CAC TTC ATC AAG GCA TAA AAGGGA TATTATAATA
Leu Met Thr Asn Ile Val Lys Asp Leu Asp Ala His Phe Ile Lys Ala ***>
___b___b___b___b___b___b___DRU1 EXON II____b___b___b___b___b___b___>

    1980       1990       2000       2010       2020       2030       2040       2050
AATCAAGCAT ATGAAACACG ATGAAAAGAG AGCTAGCCAC TATCTACTGC TGGTTTATAA GTTTAAAGAT AATCATGTGA

    >Nsi_I
     |
    2060       2070       2080       2090       2100       2110       2120       2130
     |
ACGTTGTAAT GCATGCTTTG TTTGGTTACT TCGTTTTAAT GTCTTGTTAT GCACTAATAC CGTCAGTGTA ATAAAAGCTA

                                                                          >poly(A)_site
                                                                             |
    2140       2150       2160       2170       2180       2190       2200       2210
                                                                             |
GTGTGAAAGG ATCTGATATA TTGTGATGTA TCATGTATTC AACTACCAAC TATATATGGT ATCATATTTA TATATCAAAT

AAA
```

Fig. 6B

```
        10         20         30         40         50         60         70         80
ATGCATATCA ACAACTACGA ATAAAGAGAT CAGCCTTTCC GTATCTGGTG GATGTTTGAG TCGGTGATGA CCATCTAATT

        90        100        110        120        130        140        150        160
AAAGAAAGAA GAAAAATTAT ACATATTGTG GACCTCCCCA TATATAATTC TTATCATCTT TGTTACTGCC ATTATGATTA

       170        180        190        200        210        220        230        240
TAAAATGATA TTAAAGGGAT GGTGTACCGT GTACTAATCA AATATCTACC TGATCTTATT GATTTGAAAG ATCATAAAAA

       250        260        270        280        290        300        310        320
GAAATTAAAA TTGTTCAAAA TAAACCCCTA GAATTATATA TAGTTCATTA AGTTCAAATT AATTCGTTTG AAACGTGTTA

       330        340        350        360        370        380        390        400
AGCAACCCTA CAACGTACTA AGCACCCTAG CTCCCTTTGC CTCTCGGCGG TAAGAGGAGA TATCCTCAGT CGAATTATGA

       410        420        430        440        450        460        470        480
GCCGATCGAG GAAAGCTCGA TCAGTTGGAA AATCTTTCTT TCTTATGGCC AAGTTGTTTC AAACAATATA TTGAATTATT

       490        500        510        520        530        540        550        560
GACTCTTAGC AACTTAAGTT TCAAACCGTG ACGAACCAAT AAAATTTGAC AAATTAATCA CTTTAAGTGC CTAGTGGATC

       570        580        590        600        610        620        630        640
AGCGTCTAGG TTGGGAACCC CTCTACCTGC GTTTGATTCA CCAAGCTATC AAAATGGTCA GACACTGTGC TGCAATGCAC

       650        660        670        680        690        700        710        720
AATTGGAGCA TTTCACATGC GTTGCATGAA TTATTCCTTG GGTTAGGAAA CCTTTGAAAT ACCTTGACTA AGGTAAAAAA

       730        740        750        760        770        780        790        800
AAAAACTTGA CAAATTAATA AATATTAATA TTGATTTTGT ACGTACACGA CTTAACCAAA CTCTCAATGA TTTATTGATT

       810        820        830        840        850        860        870        880
TCTAATATAT ATATTAATAA CGTACGTCTA ATTGGATCAT TCATGATCTA CAGCCATCAC ATCTCAGATG ATTTTCTTGC

       890        900        910        920        930        940        950        960
AATGAATTGC CTAAGCTGGC GTTATTATCT TTTTTTCATA ATACAGTTTT AAAAAAGGGT ACGTATTGGA GCTGGTGATG

       970        980        990       1000       1010       1020       1030       1040
ACTTCTTAAG AAACAACAAA TTAACGCCAT AGCTATTTGA TTTATATATC CAAAAGGAGA AAATGTATAA GATCGTTGCT

                                                       >CAAT_box
      1050       1060       1070       1080       1090 |     1100       1110       1120
TACTTAATTT GCAGGCTAGG TTAATTGACA TCAAATAATT GAAGAGTACG TAGGGCCAAT GTTGCTGAGA TCTAGCATCA
```

Fig. 7A

```
         1130      1140      1150      1160      1170      1180      1190      1200
    *    *    *    *    *    *    *    *    *    *    *    *    *    *    *    *
ATAATAGGAT TTGGCTTGTC GATCGATCAT CTTTATTTAA TTGAGAGGTA TGTATCCATA TGTTTTCTGA AATTAAAATA

                                                    >TATA_box
                                                         |
         1210      1220      1230      1240      1250      1260      1270      1280
    *    *    *    *    *    *    *    *    *    *    *  | *    *    *    *    *
TTACCTAATA ATTGAGCTGA AACTGTAGTG AATTTAACCT TTTCTAAGTT CTGCCCATAT ATAACATACC ACATAGGTAG

                >TATA_box
                   |
         1290      |1300      1310      1320      1330      1340      1350
    *    *    *    |    *    *    *    *    *    *    *    *    *    *    *
CTGATCGATC GATCATATAT ATGTACTTAG GGTTCTGATC AGTATCAATA TCGATCACAA GTGCTGATAA TTAAAC
```

Fig. 7B

```
TAAGTTCTGC CCATATATAA CATACCACAT AGGTAGCTGA TCGATCGATC ATATATATGT  60
ACTTAGGGTT CTGATCAGTA TCAATATCGA TCACAAGTGC TGATAATTAA AC         112
```

Fig. 8

```
AATGTTGCTG AGATCTAGCA TCAATAATAG GATTTGGCTT GTCGATCGAT CATCTTTATT  60
TAATTGAGAG GTATGTATCC ATATGTTTTC TGAAATTAAA ATATTACCTA ATAATTGAGC 120
TGAAACTGTA GTGAATTTAA CCTTTTCTAA GTTCTGCCCA TATATAACAT ACCACATAGG 180
TAGCTGATCG ATCGATCATA TATATGTACT TAGGGTTCTG ATCAGTATCA ATATCGATCA 240
CAAGTGCTGA TAATTAAAC
```

Fig. 9

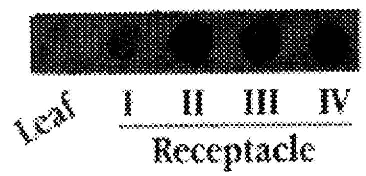
Fig. 14
Fig. 15
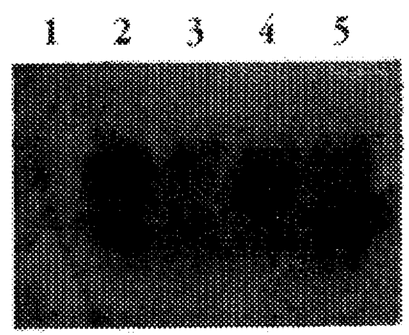
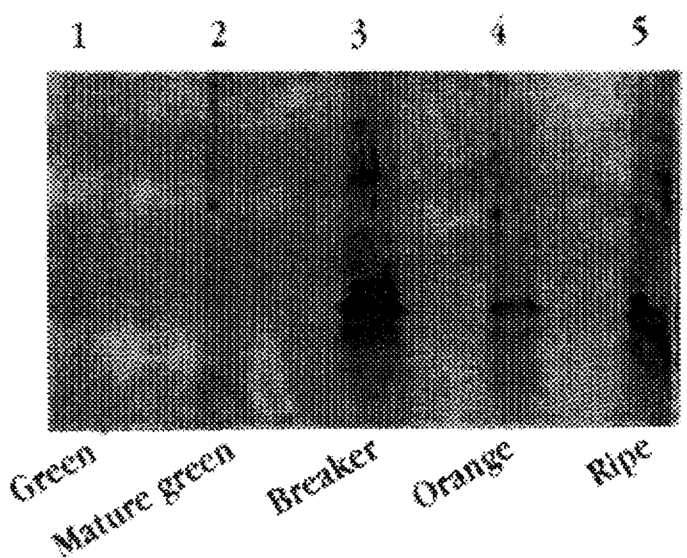
Fig. 16

RASPBERRY PROMOTERS FOR EXPRESSION OF TRANSGENES IN PLANTS

This application is a continuation-in-part of U.S. patent application Ser. No. 08/592,936, filed on 29 Jan. 1996, herein incorporated by reference.

FIELD OF THE INVENTION

The present invention relates to the identification of promoters from raspberry which are capable of providing constitutive expression of heterologous plant genes, and to chimeric genes, cassette vectors, kits, transgenic plants, and methods employing such promoters.

REFERENCES

Adams, D. O., and Yang, S. F., *Plant Physiology* 70:117–123 (1977).

Akama, K. et al., *Plant Cell Reports* 14(7):450–454 (1995).

Ausubel, F. M., et al., in CURRENT PROTOCOLS IN MOLECULAR BIOLOGY, John Wiley and Sons, Inc., Media Pa. (1992).

Balazs, E., et al., *Gene* 19(3):239–249 (1982).

Beachy, R., et al., *Annu. Rev. Phytopathol.* 28:451–74 (1990).

Beck, et al., *Gene* 19:327–336 (1982).

Bellini, C., et al., *Bio/Technol* 7(5):503–508 (1989).

Benfey, P. N., et al., *Science* 250:959–966 (1990).

Benvenuto, E., et al., XXIst Annual Meeting of the Italian Society for Agricultural Genetics, Como, Italy, Sep. 30–Oct. 2, 1987 *Genet. Agrar.* 42(1) (1988).

Bestwick, R. K., et al., PCT International Publication No. WO 95/35387, published 28 Dec. 1995.

Brunke, K. J. and Wilson, S. L., European Patent Publication No. 0 559 603 A2, published Sep. 08, 1993.

Comai, L. and Coning, A. J., U.S. Pat. No. 5,187,267, issued 16 Feb., 1993.

Cordes, S., et al., Plant Cell 1:1025–1034 (1989).

Dayhoff, M.O., in ATLAS OF PROTEIN SEQUENCE AND STRUCTURE Vol. 5, National Biomedical Research Foundation, pp. 101–110, and Supplement 2 to this volume, pp. 1–10 (1972).

Deikman, J., et al., EMBO J. 7:3315 (1988).

Deikman, J., et al., *Plant Physiol.* 100:2013 (1992).

Delanney, X., et al., Crop Science 35(5):1461–1467 (1995).

Doyle, J. J., and Doyle, J. L., *Focus* 12:13–15 (1990).

Ferro, A., et al., U.S. Pat. No. 5,416,250, issued 16 May 1995.

Fillatti, J., et al., *Biotechnology* 5:726–730 (1987).

Fraley, R., et al., U.S. Pat. No. 5,352,605, issued on October 4, 1994.

Fry, J., et al., *Plant Cell Reports* 6:321:325 (1987).

Gritz, L., et al., *Gene* 25:179–188 (1983).

Guilley, H., et al., *Cell* 30(3):763–773 (1982).

Hood, E., et al., *J. Bacteriol.* 168:1291–1301 (1986).

Hooykaas, P. J. J., and Schilperoot, R. A., TRENDS IN BIOCHEMICAL SCIENCES., International Union of Biochemistry and Elsevier Science Publishers, v. 10(8):307–309 (Aug. 1985).

Hughes, J. A., et al., *J. Bact.* 169:3625–3632 (1987).

Jefferson, R. A., et al., *EMBO J.* 6:3901 (1987a).

Jefferson, R. A., *Plant Mol. Biol.* Rep. 5:387 (1987b).

Jongedijk, E., et al., *Euphytica* 85:173–180 (1995).

Kawasaki, E. S., et al., in PCR TECHNOLOGY: PRINCIPLES AND APPLICATIONS OF DNA AMPLIFICATION (H. A. Erlich, Ed.) Stockton Press (1989).

Klein, T. M., et al., *PNAS (USA)* 85(22):8502–8505 (1988).

Laemelli, U. K., *Nature* 227:680–685 (1970).

Lee, J.J., et al., *Meth. of Enzymol.* 152:633–648 (1987).

Leisner, S. M., and Gelvin, S. B., *Proc. Natl. Acad. Sci. USA* 85(8):2553–2557 (1988).

Maniatis, T., et al., in MOLECULAR CLONING: A LABORATORY MANUAL, Cold Spring Harbor Laboratory (1982).

Melchers, L. S., et al., *Plant J.* 5:469–480 (1994).

Miki, B. L. A., et al., PLANT DNA INFECTIOUS AGENTS (Hohn, T., et al., Eds.) Springer-Verlag, Wien, Austria, pp.249–265 (1987).

Mullis, K. B., U.S. Pat. No. 4,683,202, issued 28 Jul. 1987.

Mullis, K. B., et al., U.S. Pat. No. 4,683,195, issued 28 Jul. 1987.

Nagel, R., et al., *FEMS Microbiol. Lett.* 67:325 (1990).

Ni, M., et al., *Plant J.* 7:661–676 (1995).

Odell, J. T., et al., *Nature* 313:810–812 (1985).

Odell, J.T., et al., *J. Cell Biochem. (Suppl.* 11B):60 (1987).

Odell, J. T., et al., *Plant Mol Biol* 10(3):263–272 (1988).

Ochman, et al., PCR PROTOCOLS: A GUIDE TO METHODS AND APPLICATIONS, XVIII, Academic Press, Inc., San Diego Calif., USA and London, England p. 219–227 (1990).

Pearson, W. R., *Methods in Enzymology* 183:63–98 (1990).

Pearson, W. R. and Lipman, D. J., *PNAS* 85:2444–2448 (1988).

Picton, S., et al., *Plant Physiology* 103(4): 1471–1472 (1993).

Ponstein, A. S., et al., *Plant Physiology* 104:109–118 (1994).

Rogers, S., U.S. Pat. 5,034,322, issued on Jul. 23, 1991.

Rogers, S., U.S. Pat. No. 5,378,619, issued on Jan. 3, 1995.

Saiki, R. K., et al., Science 239:487–491 (1988).

Sambrook, J., et al., in MOLECULAR CLONING: A LABORATORY MANUAL, Cold Spring Harbor Laboratory Press, Vol. 2 (1989).

Stalker, D., et al., *Science* 242:419–423 (1988).

Tinius, C. N., et al., *Crop Science* 35(5):1451–1461 (1995).

Toubart, P., et al., *Plant J.* 3:367–373 (1992).

Tommerup, H., et al., *Eur. Congr. Biotechnol.* 5:916–918 (1990).

Van Den Elzen, P. L. M., et al. "Virus and Fungal Resistance: From Laboratory to Field" in: THE PRODUCTION AND USES OF GENETICALLY TRANSFORMED PLANTS (Bevan, M. W., et al., Eds), Royal Society Discussion Meeting, Chapman and Hall Ltd., London England, 1994.

Veluthambi, K., et al., *J. Bacteriol.* 170(4):1523–1532 (1988).

Wang, A. M., et al. in PCR PROTOCOLS: A GUIDE TO METHODS AND APPLICATIONS (M. A. Innis, et al., Eds.) Academic Press (1990).

Woloshuk, C. P., et al., *J. Plant Cell* 3:619–628 (1991).

Yao, J. L., et al., *Plant Cell Reports* 14(7): 407–412 (1995).

Zhou, H., et al., *Plant Cell Reports* 15:159–163 (1995).

Zhu, Q., et al., *Plant Cell* 7:1681–1689 (1995).

BACKGROUND OF THE INVENTION

Promoters that regulate gene expression in plants are essential elements of plant genetic engineering. Several examples of promoters useful for the expression of selected genes in plants are now available (Zhu, et al., 1995; Ni, et al., 1995).

To be expressed in a cell, a gene must be operably linked to a promoter which is recognized by certain enzymes in the cell. The 5' non-coding regions of a gene (i.e., regions immediately 5' to the coding region), referred to as promoters or transcriptional regulatory regions, initiate transcription of the gene to produce a mRNA transcript. The mRNA is then translated at the ribosomes of the cell to yield an encoded polypeptide.

Promoters typically contain from about 500–1500 bases, and can provide regulated expression of genes under their control. A promoter used for expressing a heterologous gene in plant cells may be characterized as (i) a constitutive promoter, that is, a promoter capable of causing similar levels of gene expression in all or many plant tissues, or, (ii) a tissue selective promoter, that is, one which is capable of regulating gene expression to select tissues in a plant transformant (e.g., leaves or fruit).

Many such promoters have been characterized, including those derived from plant viruses, Agrobacterium genes, and a variety of plant genes. Considerable effort has gone into the isolation and characterization of constitutive promoters to drive the expression of a variety of heterologous genes in plant systems.

Viral promoters (i.e., promoters from viral genes) for expressing selected genes in plants, have been identified in the caulimovirus family of viruses (a group of double-stranded DNA viruses), and include the Cauliflower Mosaic Virus (CaMV) 35S (Balazs, et al, 1982; Guilley, et al., 1982; Odell, et al., 1985; Odell, et al., 1987; Odell, et al., 1988; Tommerup, et al., 1990; Jefferson, et al., 1987a; Jefferson, 1987b) and CAMV 19S promoters (Fraley, et al., 1994), and the Figwort Mosaic Virus (FMV) (Rogers, 1995) promoter. Promoters useful for regulating gene expression in plants and obtained from bacterial sources, such as Agrobacterium-derived promoters, have been identified and isolated. Such promoters include those derived from Agrobacterium T-DNA opine synthase genes, and include the nopaline synthase (nos) promoter (Rogers, 1991), the octopine synthase (ocs) promoter (Leisner and Gelvin, 1988) and mannopine synthase (mas) promoter.

Plant promoters (promoters derived from plant sources) effective to provide constitutive expression, are less well known, and include hsp80, Heat Shock Protein 80 from cauliflower, (Brunke and Wilson, 1993), and the tomato ubiquitin promoter (Picton, et al., 1993). These promoters can be used to direct the constitutive expression of heterologous nucleic acid sequences in transformed plant tissues. At present, a relatively small number of plant promoters, particularly constitutive plant promoters, has been identified. The use of such promoters in plant genetic engineering has been rather limited to date, since gene expression in plants is, for the most part, typically tissue, developmentally, or environmentally-regulated.

SUMMARY OF THE INVENTION

The present invention is directed to raspberry promoters which separately and in combination provide moderate-level, constitutive expression of nucleic acid sequences placed under their control. The promoters of the invention can also confer constitutive expression on heterologous, non-constitutive promoters.

The present invention is directed to a promoter which, in a native raspberry genome, is operably linked to the coding region of a dru1 gene. Chimeric genes of the present invention contain a DNA sequence encoding a product of interest under the transcriptional control of a raspberry dru1 promoter. The DNA sequence is typically heterologous to the promoter and is operably linked to the promoter to enable constitutive expression of the product.

In one embodiment, the product is a polypeptide that permits selection of transformed plant cells containing the chimeric gene by rendering such cells resistant to an amount of an antibiotic that would be toxic to non-transformed cells. Exemplary products include, but are not limited to, aminoglycoside phosphotransferases, such as neomycin phosphotransferase and hygromycin phosphotransferase. In one such embodiment, a chimeric gene of the invention contains an hpt gene sequence encoding hygromycin phosphotransferase II under the transcriptional control of a dru1 promoter. In an alternate embodiment, a chimeric gene of the invention contains an nptII gene sequence encoding neomycin phosphotransferase under the transcriptional control of a dru1 promoter.

In another embodiment, the product is a polypeptide that confers herbicide-resistance to transformed plant cells expressing the polypeptide. In one such embodiment, a chimeric gene of the present invention contains a bxn gene encoding a bromoxynil-specific nitrilase under the transcriptional control of a dru1 promoter. Transformed plants containing this chimeric gene express a bromoxynil-specific nitrilase and are resistant to the application of bromoxynil-containing herbicides. Other exemplary DNA sequences encoding genes conferring herbicide resistance include the EPSP synthase gene (encoding 5-enolpyruvylshikimate-3-phosphate synthase enzyme), which confers resistance to glyphosate; an acetolactate synthase gene, which confers resistance to the herbicide "GLEAN"; a bialaphos resistance gene (the bar gene) coding for phosphinothricin acetyltransferase (PAT), and the glyphosate-tolerant genes, CP4 and GOX. Chimeric genes of the invention contain one or more of these herbicide-resistance genes, operationally linked to a dru1 promoter.

In another embodiment, the DNA sequence or cDNA sequence encodes a viral coat protein, such as alfalfa mosaic virus coat protein, cucumber mosaic virus coat protein, tobacco streak virus coat protein, potato virus coat protein, tobacco rattle virus coat protein, and tobacco mosaic virus coat protein. According to one such embodiment, a chimeric gene of the invention contains a viral coat protein gene, such as ALMV, CMV, TSV, PVX, TRV, or TMV, under the transcriptional control of a dru1 promoter. Alternatively, the DNA sequence corresponds to a gene encoding a dominant defective protein, such as mutant forms of the ETR1 gene which confer ethylene insensitivity. In yet another embodiment, the DNA sequence corresponds to a gene capable of altering a plant biochemical pathway, such as such as the ACCD gene. The ACCD gene forms a product which degrades a precursor in the ethylene biosynthetic pathway.

In another aspect, the invention includes an isolated DNA molecule comprising a constitutive promoter from a raspberry dru1 gene. One exemplary raspberry dru1 Opromoter is the dru110 promoter, presented herein as SEQ ID NO:3. Another exemplary constitutive raspberry promoter is the dru259 promoter, presented as SEQ ID NO:4. Additional fragments may be derived from the sequence representing the full-length dru1 promoter, SEQ ID NO:2, where the smaller fragments are effective to regulate constitutive expression of a DNA sequence under their control.

The present invention also includes the use of any of the above chimeric genes, DNA constructs, and isolated DNA sequences to generate a plant transformation vector. Such vectors can be used in any plant cell transformation method, including Agrobacterium-based methods, electroporation, microinjection, and microprojectile bombardment. These vectors may also form part of a plant transformation kit. Other components of the kit may include, but are not limited to, reagents useful for plant cell transformation.

In another embodiment, the present invention includes a plant cell, plant tissue, transgenic plant, fruit cell, whole fruit, seeds or calli containing any of the above-described raspberry promoters, chimeric genes or DNA constructs.

In another aspect of the present invention, the dru promoters described herein are employed in a method for providing moderate expression of a heterologous gene, such as a selectable marker gene, in transgenic plants. In this method, a chimeric gene of the present invention containing a DNA sequence encoding a selectable marker product (e.g., a neomycin phosphotransferase or hygromycin phosphotransferase) is introduced into progenitor cells of a plant. Transgenic plants containing the chimeric gene are selected by their ability to grow in the presence of an amount of selective agent (e.g., hygromycin, geneticin or kanamycin) that is toxic to non-transformed cells. The transformed plant cells thus selected are then regenerated to provide a differentiated plant, followed by selection of a transformed plant which expresses the product.

Further, the invention includes a method for producing a transgenic fruit-bearing plant. In this method the chimeric gene of the present invention, typically carried in an expression vector allowing selection in plant cells, is introduced into progenitor cells of selected plant. These progenitor cells are then grown to produce a transgenic plant.

The method may further comprise isolation of a dru1 promoter (such as dru110 or dru259) by the following steps:

(i) selecting a probe DNA molecule containing a sequence homologous to a region of raspberry dru1 gene DNA, (ii) contacting the probe with a plurality of target DNA molecules derived from a raspberry genome under conditions favoring specific hybridization between the probe molecule and a target molecule homologous to the probe molecule, (iii) identifying a target molecule having a DNA sequence homologous to the raspberry dru1 gene, and (iv) isolating promoter sequences associated with the target molecule, and (v) evaluating one or more of the isolated sequences or portion thereof for its ability to regulate constitutive expression of a downstream gene under its control.

The chimeric genes, vectors, constructs, isolated DNA molecules, products and methods of the present invention can be produced using the raspberry dru1 promoter sequences essentially as described above.

These and other objects and features of the invention will become more fully apparent when the following detailed description is read in conjunction with the accompanying figures and examples.

BRIEF DESCRIPTION OF THE FIGURES

FIGS. 6A and 6B present the genomic DNA sequence of the dru1 gene (SEQ ID NO:1). Indicated in the figures are a CAAT box, TATA box, ATG start codon, two exons, an intron, splicing sites, a stop codon and poly-adenylation sites;

FIGS. 7A and 7B present the DNA sequence of the full length dru1 promoter (SEQ ID NO:2);

FIG. 8 presents the DNA sequence of the dru110 promoter (SEQ ID NO:3);

FIG. 9 presents the DNA sequence of the dru259 promoter (SEQ ID NO:4);

FIG. 14 shows the results of RNA dot blot analysis of dru1 RNA expression in raspberry leaf and receptacle. RNA was isolated from green, mature green, breaker & orange/ripe raspberries (corresponding to stages I, II, III, IV, respectively);

FIG. 15 shows the results of a RNA hybridization study evaluating the expression of dru1 RNA in raspberry leaf and fruit;

FIG. 16 shows the results of polyacrylamide gel electrophoretic analysis of raspberry drupelet proteins obtained from drupelets at various stages of ripening.

DETAILED DESCRIPTION OF THE INVENTION

I. Definitions

Figure 1:
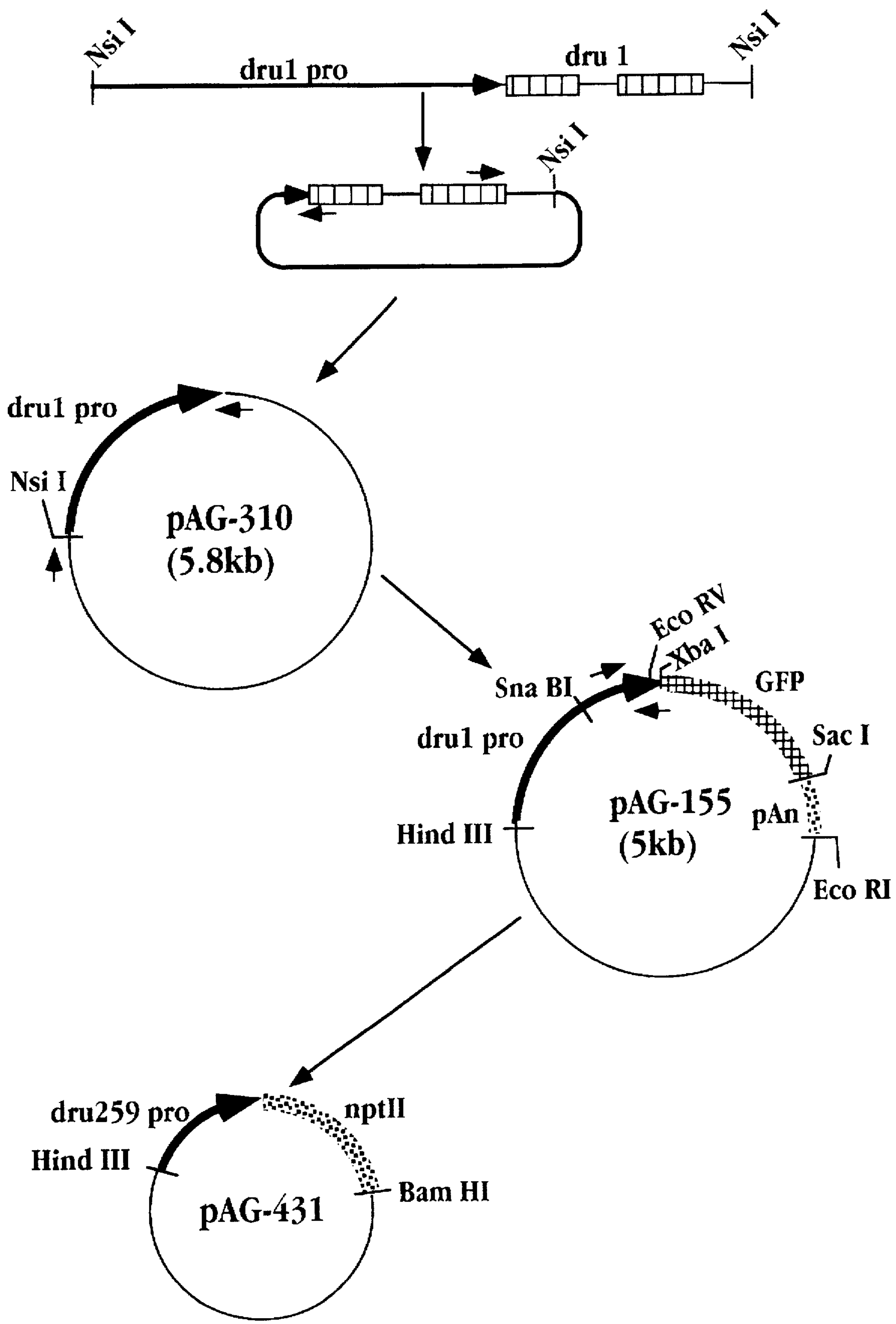
FIG. 1 is a schematic diagram illustrating the creation of plasmid pAG-431 containing an exemplary raspberry dru1 promoter, referred to herein as dru259 pro, and the nptII gene.

The following terms, as used herein, have the meanings as indicated:

"Chimeric gene" as defined herein refers to a nonnaturally occurring gene which is composed of parts of different genes. A chimeric gene is typically composed of a promoter sequence operably linked to a "heterologous" DNA sequence. A typical chimeric gene of the present invention, for transformation into a plant, will include a raspberry dru promoter (e.g., a dru110 or dru259 promoter), a heterologous structural DNA coding sequence (e.g., the aminoglycoside phosphotransferase (nptII) gene) and a 3' non-translated polyadenylation site.

A "constitutive" promoter refers to a promoter that directs RNA production in many or all tissues of a plant transformant, as opposed to a tissue-specific promoter, which directs RNA synthesis at higher levels in particular types of cells and tissues (e.g., fruit specific promoters such as the tomato E4 or E8 promoter (Cordes, et al., 1989; Bestwick, et al., 1995).

By "promoter" is meant a sequence of DNA that directs transcription of a downstream heterologous gene, and includes promoters derived by means of ligation with operator regions, random or controlled mutagenesis, addition or duplication of enhancer sequences, addition or modification with synthetic linkers, and the like.

By "plant promoter" is meant a promoter (as defined above), which in its native form, is derived from plant genomic DNA.

"Raspberry promoter" refers to a promoter (as defined above) which, in its native form, is derived from a raspberry genome. For example, a dru1 promoter, such as drullo or dru259, is a non-coding regulatory region which is operably linked, in a native raspberry genome, to the coding region of a dru1 gene.

A raspberry promoter derived from a specified gene (e.g., a raspberry promoter derived from the dru1 gene, such as dru110 or dru259) includes a promoter in which at least one or more regions of the promoter are derived from the specified raspberry gene. An exemplary promoter of this type is one in which a region of the promoter (e.g., a dru259 promoter) is replaced by one or more sequences derived from a different gene, without substantially reducing the expression of the resulting chimeric gene in a host cell, or altering the function of the unaltered dru259 promoter.

"Promoter strength" refers to the level of promoter-regulated (e.g, dru110, dru259) expression of a heterologous gene in a plant tissue or tissues, relative to a suitable standard (e.g., caulimovirus cassava mottle vein virus promoter CAS or the hsp80 promoter). Expression levels can be measured by linking the promoter to a suitable reporter gene such as GUS (β-glucuronidase), dihydrofolate reductase, or nptII (neomycin phosphotransferase). Expression of the reporter gene can be easily measured by fluorometric, spectrophotometric or histochemical assays (Jefferson, et al., 1987a; Jefferson, 1987b).

For the purposes of the present invention, a moderate promoter is one that drives expression of a reporter gene at about 10–90% of the level obtained with a promoter such as hsp80.

A "heterologous" DNA coding sequence is a structural coding sequence that is not native to the plant being transformed, or a coding sequence that has been engineered for improved characteristics of its protein product.

Heterologous, with respect to the promoter, refers to a coding sequence that does not exist in nature in the same gene with the promoter to which it is currently attached.

A gene considered to share sequence identity with the dru1 gene, or a particular region or regions thereof, has at least about 60% or preferably 80% global sequence identity over a length of polynucleotide sequence corresponding to the raspberry dru1 polynucleotide sequences disclosed herein (e.g., SEQ ID NOs:1–4).

"Sequence identity" is determined essentially as follows. Two polynucleotide sequences of the same length (preferably, corresponding to the coding sequences of the gene) are considered to be identical (i.e., homologous) to one another, if, when they are aligned using the ALIGN program, over 60% or preferably 80% of the nucleic acids in the highest scoring alignment are identically aligned using a ktup of 1, the default parameters and the default PAM matrix (Dayhoff, 1972).

The ALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

Two nucleic acid fragments are considered to be "selectively hybridizable" to a polynucleotide derived from a dru1 gene if they are capable of specifically hybridizing to the coding sequences or a variants thereof or of specifically priming a polymerase chain amplification reaction: (i) under typical hybridization and wash conditions, as described, for example, in Maniatis, et al., 1982, pages 320–328, and 382–389; (ii) using reduced stringency wash conditions that allow at most about 25–30% basepair mismatches, for example: 2×SSC (contains sodium 3.0M NaCl and 0.3M sodium citrate, at pH 7.0), 0.1% sodium dodecyl sulfate (SDS) solution, room temperature twice, 30 minutes each; then 2×SSC, 0.1% SDS, 37° C., once, for 30 minutes; then 2×SSC, at room temperature twice, for 10 minutes each, or (iii) selecting primers for use in typical polymerase chain reactions (PCR) under standard conditions (for example, in Saiki, et al., 1988), which result in specific amplification of sequences of the desired target sequence or its variants.

Preferably, highly homologous nucleic acid strands contain less than 20–40% basepair mismatches, even more preferably less than 5–20% basepair mismatches. These degrees of homology (i.e., sequence identity) can be selected by using wash conditions of appropriate stringency for identification of clones from gene libraries (or other sources of genetic material), as is well known in the art.

A "dru1 encoded polypeptide" is defined herein as any polypeptide homologous to (i.e., having essentially the same sequence identity as) a dru1 encoded polypeptide. In one embodiment, a polypeptide is homologous to a dru1 encoded polypeptide if it is encoded by nucleic acid that selectively hybridizes to sequences of dru1 or its variants.

In another embodiment, a polypeptide is homologous to a dru1 encoded polypeptide if it is encoded by dru1 or its variants, as defined above. Polypeptides of this group are typically larger than 15, preferable 25, or more preferable 35, contiguous amino acids. Further, for polypeptides longer than about 60 amino acids, sequence comparisons for the purpose of determining "polypeptide homology" or "polypeptide sequence identity" are performed using the local alignment program LALIGN. The polypeptide sequence is compared against the dru1 amino acid sequence or any of its variants, as defined above, using the LALIGN program with a ktup of 1, default parameters and the default PAM.

Any polypeptide with an optimal alignment longer than 60 amino acids and greater than 55% or preferably 80% of identically aligned amino acids is considered to be a "homologous polypeptide." The LALIGN program is found in the FASTA version 1.7 suite of sequence comparison programs (Pearson and Lipman, 1988; Pearson, 1990; program available from William R. Pearson, Department of Biological Chemistry, Box 440, Jordan Hall, Charlottesville, Va.).

A polynucleotide is "derived from" dru1 if it has the same or substantially the same basepair sequence as a region of the dru1 protein coding sequence, cDNA of dru1 or complements thereof, or if it displays homology as defined above.

A polypeptide or polypeptide "fragment" is "derived from" dru1 if it is (i) encoded by a dru1 gene, or (ii) displays homology to dru1 encoded polypeptides as noted above.

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

As used herein, a "plant cell" refers to any cell derived from a plant, including undifferentiated tissue (e.g., callus) as well as plant seeds, pollen, progagules and embryos.

II. Identification and Isolation of a Raspberry dru1 Promoter

The present invention relates, in one aspect, to a promoter which, in a native raspberry genome, (i) is operably linked to the coding region of a dru1 gene, and (ii) functions as a moderate strength, constitutive promoter. This aspect of the invention is based upon the discovery of the dru1 gene in raspberries, which is expressed at very high levels in ripening fruit. Expression directed by the full length dru1 promoter is fruit specific, and active during fruit ripening, as disclosed in co-owned U.S. patent application Ser. No. 08/592,936, filed on 29 Jan. 1996.

In contrast to the functional activity of the dru1 promoter, it has unexpectedly been discovered that two new promoters, both derived from the full length raspberry dru1 promoter, i) function as constitutive promoters (i.e., are not fruit-specific), and (ii) drive expression of genes under their control at moderate levels, as will be described in more detail below.

The identification of the dru1 gene from raspberries, as well as the isolation of two exemplary dru1 promoters of the present invention, dru110 and dru259, will now be described. 19

A. dru1 Protein Identification. Purification and Sequence Determination

Figure 10:
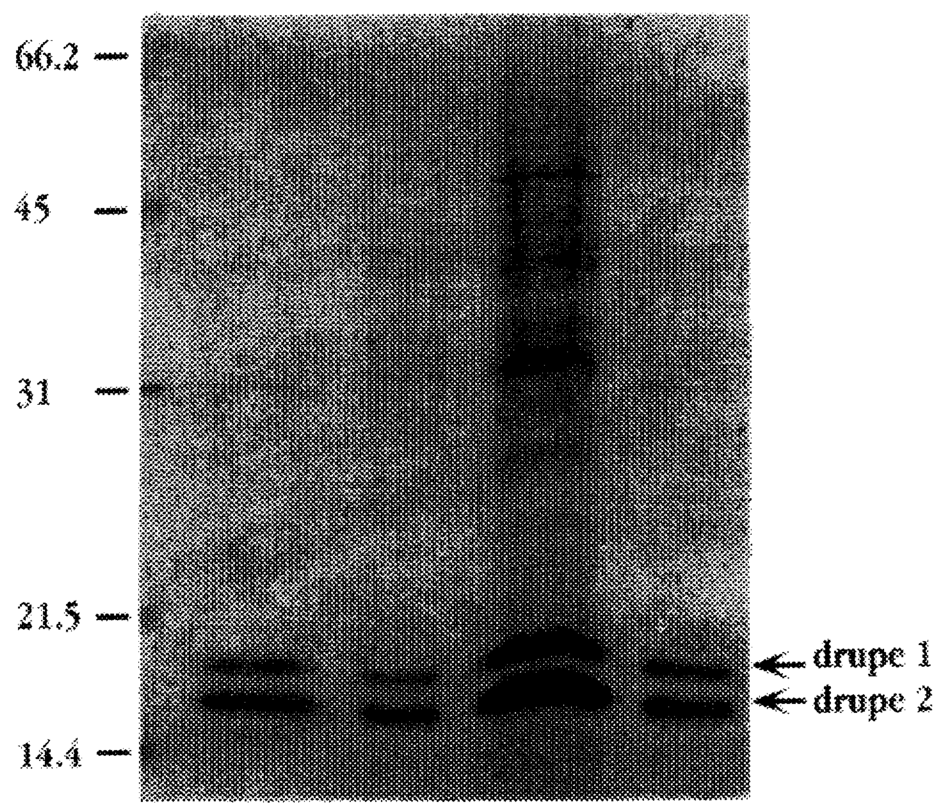
FIG. 10 presents representative results of polyacrylamide gel electrophoretic analysis of raspberry drupelet proteins.

Protein(s) produced by ripening fruit, such as those produced by raspberry, are typically analyzed by gel electrophoresis. A coomassie blue-stained SDS polyacrylamide gel of soluble drupelet proteins is shown in FIG. 10 (Examples 1A–B). As can be seen from FIG. 10, two highly abundant proteins isolable from raspberries are observed at approximately 17 and 15 kd, and are referred to herein as drupe1 and drupe2, respectively. The amount of drupe1 and drupe2 relative to the total amount of soluble protein can be determined, for example, by scanning densitometry. Scanning densitometry analysis of the gel illustrated in FIG. 10 indicates that drupel and drupe2 comprise approximately 23 and 37%, respectively, of the total soluble protein in raspberry drupelets. As a result of this determination (i.e., the high levels of drupel and drupe2), purification and sequencing of drupel and drupe2 can be carried out, for example, by using a direct western blot approach.

In carrying out a western blot analysis, total drupelet proteins are western blotted to PDVF membrane (Example 1B) and the regions corresponding to drupel and drupe2 are subjected to N-terminal amino acid sequence analysis. The drupel sample yields a thirty amino acid N-terminal sequence (Example 1B). The amino terminal drupel sequence is presented herein as SEQ ID NO:11.

B. Cloning dru1 Encoding Sequences

1. RT-PCR and Cloning of a dru1 cDNA Clone.

Figure 11A:
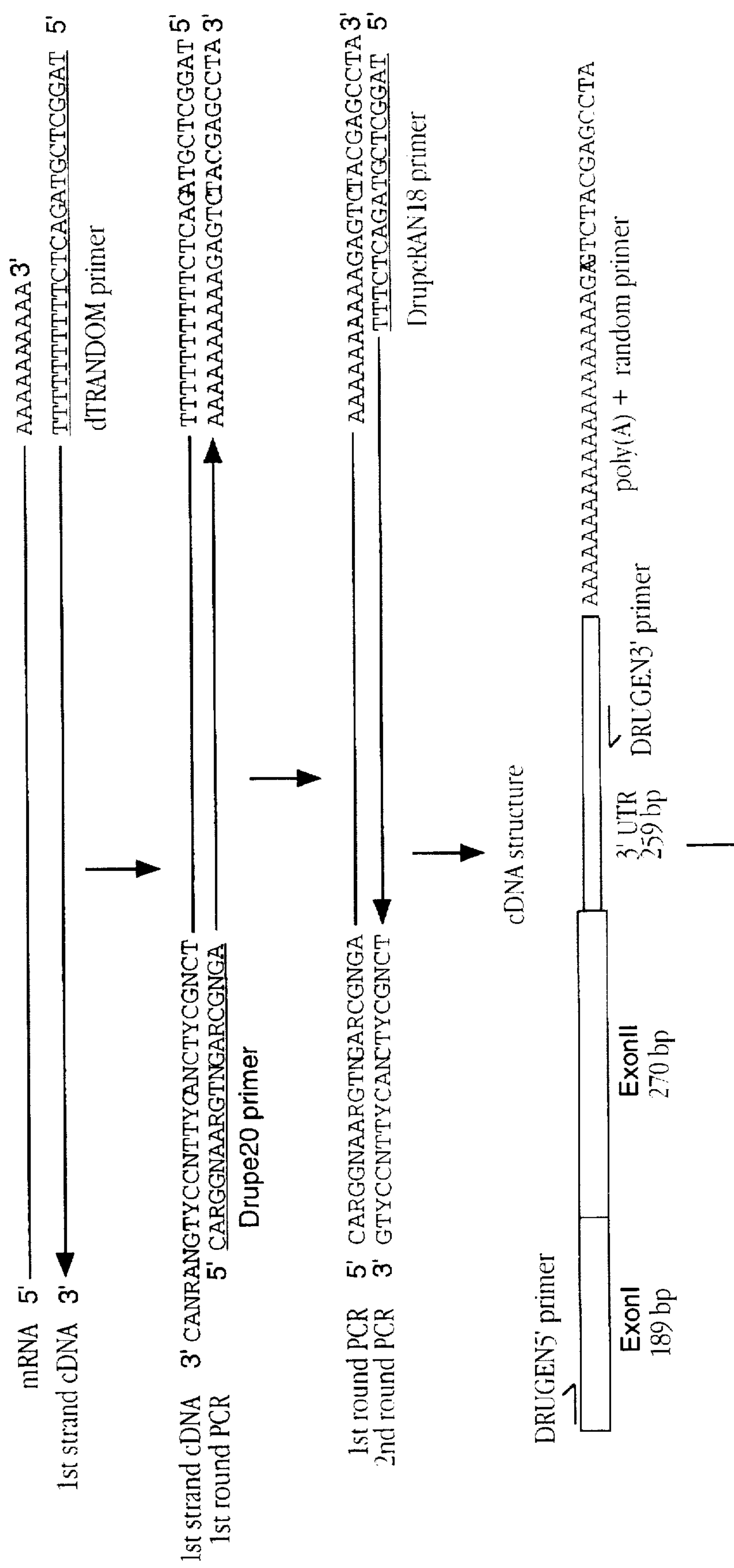
FIGS. 11A and 11B schematically represent the reverse transcriptase-polymerase chain reaction (RTPCR; Kawasaki, et al., 1989; Wang, et al., 1990) cloning of the raspberry dru1 gene; The illustrated sequences correspond to the following SEQ ID NOs: mRNA poly A tail (SEQ ID NO:21); dTRANDOM primer (SEQ ID NO:12); 1st strand cDNA, 3' end (SEQ ID NO:22); 1st round PCR, Drupe20 primer (SEQ ID NO:4); 1st round PCR, 3' end (SEQ ID NO:23); 2nd round PCR, 3' end (SEQ ID NO:24); Drupe-RAN18 primer (SEQ ID NO:15); and cDNA structure, polyA tail plus random primer (SEQ ID NO:25)
Figure 11B:
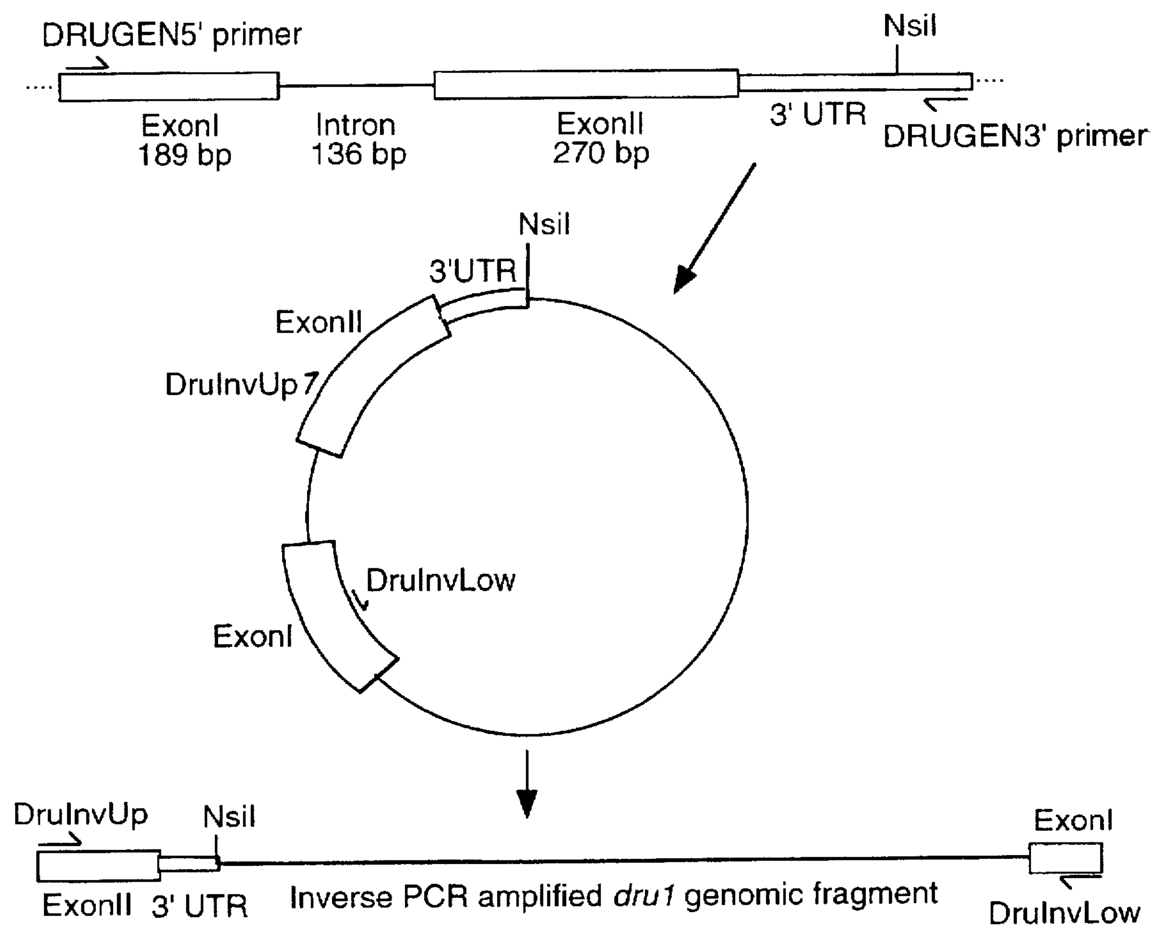

The entire procedure for cloning dru1, from cDNA synthesis to inverse PCR of a genomic copy of the gene, is shown schematically in FIGS. 11A and 11B.

In carrying out the cloning procedure, mature green raspberry drupelet mRNA is prepared as described in Example 2A and 2B and used as template in a cDNA synthesis reaction. The reaction is primed using the dTRANDOM primer (SEQ ID NO:12) shown in FIGS. 11A and 11B. The resulting cDNA (Example 2C) is subjected to a standard PCR reaction using primers corresponding to a portion of the dTRANDOM primer and a 512-fold degenerate primer (Drupe 20) based on the drupel amino terminal sequence (Example 3).

The PCR amplification products are then analyzed. Products from the above PCR reaction include a 710 bp product that is agarose gel purified and subcloned into vector pCRII (Example 3). Subsequent sequence analysis of several of these clones allows identification of those clones whose sequence encodes a protein matching the amino terminal sequence of drupel.

2. Inverse PCR Cloning of a Genomic Copy of the dru1 Gene. In this approach to cloning the dru1 gene, genomic raspberry DNA is used in a PCR reaction using primers internal to the cDNA sequence obtained as described above (Example 4). This reaction produces a genomic clone of the dru1 gene containing most of the protein coding region. A single intron was identified from the subsequent sequence analysis of this clone (FIG. 6B). An inverse PCR strategy may be employed to characterize and sequence the 5' region of the gene containing the dru1 promoter (Example 5). FIGS. 11A and 11B show schematically how this may be accomplished.

In characterizing the 5' flanking region of dru1 genomic DNA utilizing inverse PCR techniques, raspberry genomic DNA is digested with NsiI and ligated under dilute conditions to allow circularization of the restriction fragments. The ligated DNA is then subjected to PCR amplification using primers internal to the dru1 coding sequence and oriented in opposite directions from each other. This produces a PCR reaction product containing part of the first exon and 1.35 kb of the promoter. Subsequent sequence analysis of this clone in combination with sequence information from the previously described clones produces the complete dru1 sequence.

3. Sequence Determination and Evaluation of Gene Expression Patterns. The dru1 gene (FIGS. 6A, 6B) encodes a protein with the predicted amino acid sequence presented as SEQ ID NO:20. The predicted molecular weight for this protein is 17,088, which agrees closely with the 17 kd molecular weight determined by gel electrophoresis (see FIG. 10) of total drupelet protein. The dru1 protein is relatively acidic with a predicted pI of 4.8. Nucleic acid and protein homology searches of the current sequence databases can be carried out to look for significant matches. For dru1, nucleic acid and protein homology searches of the current sequence databases produced no significant matches. This result supports the original observation made with the amino terminal sequence of the protein that drupel is a novel protein.

The gene expression pattern of dru1 can be also be evaluated at the RNA and protein levels to confirm the tissue specificity of the full length promoter. Northern dot blots, FIGS. 14 and 15, of total RNA from raspberry leaf and receptacles at different ripening stages indicate a tissue and stage specific gene expression pattern. This can be confirmed by comparison of northern blots of total RNA from various other plant tissues. The tissue and stage specific gene expression pattern of dru1 was confirmed on northern blots of total RNA from leaf, receptacles, and drupelets (see FIGS. 14 and 15). In both cases, no dru1 expression is observed in leaf RNA. The RNA expression pattern in receptacles is temporally regulated while in drupelets it is fully expressed at the two stages (i.e., green and ripe) analyzed.

A protein gel of drupelet lysates from different ripening stages can also be carried out to further support stage specific expression of dru1. As illustrated in FIG. 16, electrophoretic analysis of raspberry drupelet proteins obtained from drupelets at various stages of ripening (i.e., green, mature green, breaker, orange, and ripe) further supports a stage specific expression pattern in drupelets (FIG. 16).

C. Isolation of the Full Length dru1 Promoter

Characterization of the dru1 genomic clone allows isolation of the dru1 promoter. The nucleotide sequence of an exemplary full length dru1 promoter is presented as SEQ ID NO:2.

III. Isolation of Promoters dru110 and dru259

Two representative raspberry promoters of the invention, dru110 and dru259, were isolated from the full length transcript of the dru1 promoter, which has been characterized as a stage and fruit-specific promoter. Surprisingly, these two new dru1-derived promoters have been found to function as moderate level, constitutive promoters when fused to heterologous genes and evaluated for resultant patterns of expression in transformed plants.

The truncated dru promoters, dru110 and dru259, can be obtained from the full length dru1 promoter as described in Examples 7 and 8.

Figure 2:
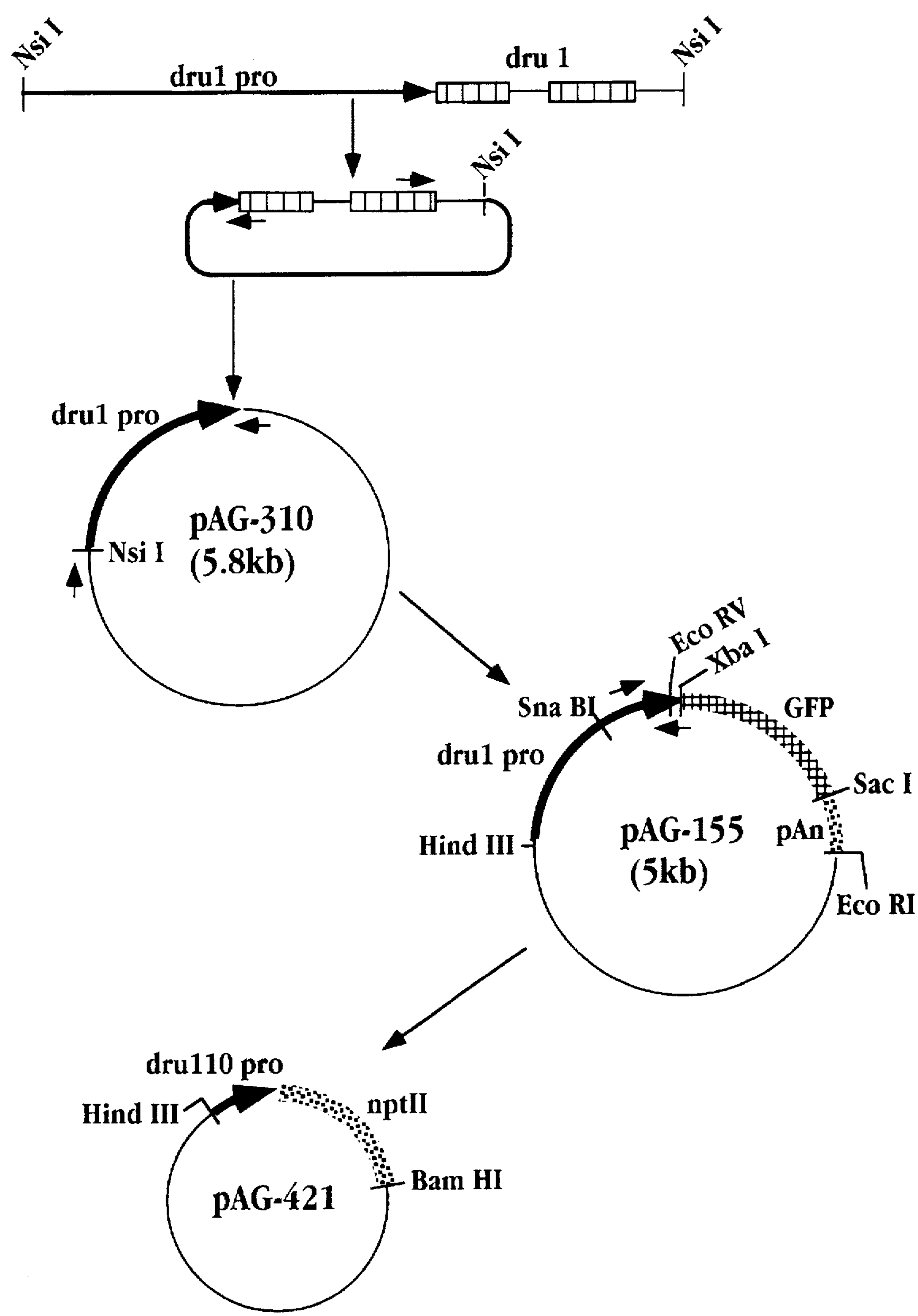
FIG. 2 is a flow chart representing the steps followed in constructing vector pAG-421 containing a chimeric dru110 pro-nptII gene.

In utilizing this approach, a PCR reaction product containing part of the first exon and 1.35 kb of the dru1 promoter (as described in section II.B.2 above) is ligated into plasmid pCRII (Invitrogen, Carlsbad, Calif.) to form a subclone, pAG-310, containing the full length dru1 promoter, as shown in FIGS. 1 and 2. A 1.3 kb DNA fragment from pAG-310 is then PCR amplified under standard conditions using primers DrupeUp (5' primer, SEQ ID NO:7) and DrupeLow (3' primer, SEQ ID NO:8).

Recovery of the amplified DNA is typically carried out by addition of solvent to the reaction mixture, followed by centrifugation, recovery of the aqueous phase, and precipitation with sodium acetate. The recovered DNA is then typically purified by centrifugation and repeated washing, followed by drying of the recovered pellet.

The 1.3 kb DNA fragment is digested to completion with restriction enzymes NsiI and XbaI, followed by purification and ligation into plant expression vector, p35S-GFP (Clontech, Palo Alto, Calif.), which has been digested with XbaI and PstI. Restriction enzymes, PstI (used to digest p35S-GFP) and NsiI (used to digest the dru1 PCR product), both generate the same 3' overhanging cohesive ends (TGCA), so that upon ligation, neither restriction site is reconstructed. The resulting intermediate plasmid, designated pAG-155, is represented schematically in FIGS. 1 and 2.

Isolation of the raspberry dru259 promoter is accomplished by digesting plasmid pAG-155 with restriction enzymes, SnaBI and EcoRV, which are both blunt end cutters, to release a 259 bp dru1 promoter fragment, referred to herein as dru259.

Isolation of the raspberry dru110 promoter is achieved by amplifying a 166 bp fragment of dru1 carried in plasmid pAG-155 using primers dru1 -118H3 (SEQ ID NO:9) and GFPStartR (SEQ ID No:lo) under standard PCR reaction conditions. The amplified product is then recovered from the reaction mixture, and purified as described above, followed by digestion of the 166 bp product with HindIII and EcoRV to produce the 112 bp promoter referred to herein as dru110.

The raspberry promoters, dru110 and dru259, can be used to regulate expression of heterologous genes. Exemplary dru promoter, dru259, has the nucleotide sequence presented herein as SEQ ID NO:4. Exemplary dru promoter, dru110, has the nucleotide sequence presented as SEQ ID NO:3.

The construction of illustrative subclones, pAG431 and pAG-421, containing nucleotide sequences corresponding to dru259 and dru110, respectively, is presented in FIGS. 1 and 2.

IV. Identification of a Plant dru1 Promoter

The present invention also provides a method for identifying and isolating a dru1 promoter, e.g. dru110 and dru259, from a variety of plant sources, e.g. raspberry. Such promoters are useful for the generation of vector constructs containing heterologous genes, such as selectable marker genes, or genes conferring herbicide resistance.

Southern blot experiments are used to demonstrate the presence of DNA molecules having significant sequence identity (i.e., typically greater than 55%, more preferably greater than 80% identity using standard sequence comparison programs) with the raspberry dru1 gene in, for example, strawberry, peach or plum. Similar Southern blot analyses may be performed on other fruit-bearing plants to identify additional dru1 genes.

Dru1 homologues are identified in a Southern blot (Ausubel, et al., 1992) of the plant genomic DNA, probed with a labelled DNA fragment containing the coding sequence of the raspberry dru1 gene.

The probe is typically selected to contain the coding sequence of dru1, rather than the promoter sequence, because coding sequences are typically more conserved from species to species than are promoter sequences. Probe molecules are generated from raspberry genomic DNA using primer-specific amplification (Mullis, 1987; Mullis, et al., 1987). The oligonucleotide primers are selected such that the amplified region includes the entire coding sequence of the raspberry dru1 gene, as provided herein. Primers may also be selected to amplify only a selected region of the raspberry dru1 gene.

Alternatively, a probe can be made by isolating restriction-digest fragments containing the sequence of interest from plasmid DNA.

The probe is labeled with a detectable moiety to enable subsequent identification of homologous target molecules. Exemplary labeling moieties include radioactive nucleotides, such as $^{32}$P-labeled nucleotides, digoxygenin-labeled nucleotides, biotinylated nucleotides, and the like, available from commercial sources.

In the case of a primer-amplified probe, labeled nucleotides may be directly incorporated into the probe during the amplification process. Probe molecules derived from DNA that has already been isolated, such as restriction-digest fragments from plasmid DNA, are typically end-labeled (Ausubel, et al., 1992).

Target molecules, such as HindIII DNA fragments from the genomes of the above-listed plants, are electrophoresed on a gel, blotted, and immobilized onto a nylon or nitrocellulose filter. Labeled probe molecules are then contacted with the target molecules under conditions favoring specific hybridization between the probe molecules and target molecules homologous to the probe molecules (Maniatis, et al., 1982; Sambrook, et al., 1989; Ausubel, et al., 1992).

Following the identification of plants containing dru1 genes, the DNA containing the desired genes, including the promoter regions, may be isolated from the respective species, by, for example, the methods described herein for the isolation of the raspberry dru1 gene. Generation of truncated promoters may be accomplished by, for example, 5' deletions such as those described herein for the isolation of the dru110 and dru259 promoters.

Variants of the dru1 promoter may be isolated from different raspberry cultivars and from other plants by the methods described above. A reporter gene, such as GUS (β-glucuronidase), can be used to test tissue for constitutive, moderate level expression regulated by such promoters. Expression of GUS protein can be easily measured by fluorometric, spectrophotometric or histochemical assays (Jefferson, et al., 1987a; Jefferson, 1987b).

Further, using chimeric genes containing dru1 promoter sequences operably linked to reporter gene sequences, DNA sequences corresponding to regulatory domains can be identified using, for example, deletion analysis (Benfey, et al., 1990). For example, the dru259 promoter sequence presented as SEQ ID NO:4 can be functionally linked to the GUS reporter gene. Deletion analysis can then be carried out by standard methods (Ausubel, et al., 1992; Maniatis, et al., 1982; Sambrook, et al., 1989). Alternatively, regions of the full length dru1 promoter sequence can be amplified using sequence-specific primers in PCR, as illustrated in FIGS. 1 and 2. These amplified fragments can then be inserted 5' to the GUS coding sequences and the resulting expression patterns evaluated for moderate level, constitutive expression, which are features of the raspberry promoters of the invention.

V. Plant Transformation

In support of the present invention, exemplary chimeric genes containing a raspberry plant promoter sequence operably linked to a heterologous DNA sequence, were constructed. Exemplary chimeric gene constructs include dru110 pro:nptII (Example 10) and dru259pro:nptII (Example 9). The protein expressed by the nptII gene, neomycin phosphotransferase, is an aminoglycoside phosphotransferase, which confers kanamycin resistance to transgenic plants expressing the product. This protein, as well as other selectable marker products, and products conferring herbicide resistance, may function more efficiently if expressed (i) constitutively, and (ii) at moderate levels (rather than being overexpressed) in transgenic plants. Accordingly, exemplary promoters dru110 and dru259 represent ideal promoters for satisfying this objective.

A. Construction of Agrobacterium Binary Plant Transformation Vectors

Figure 3:
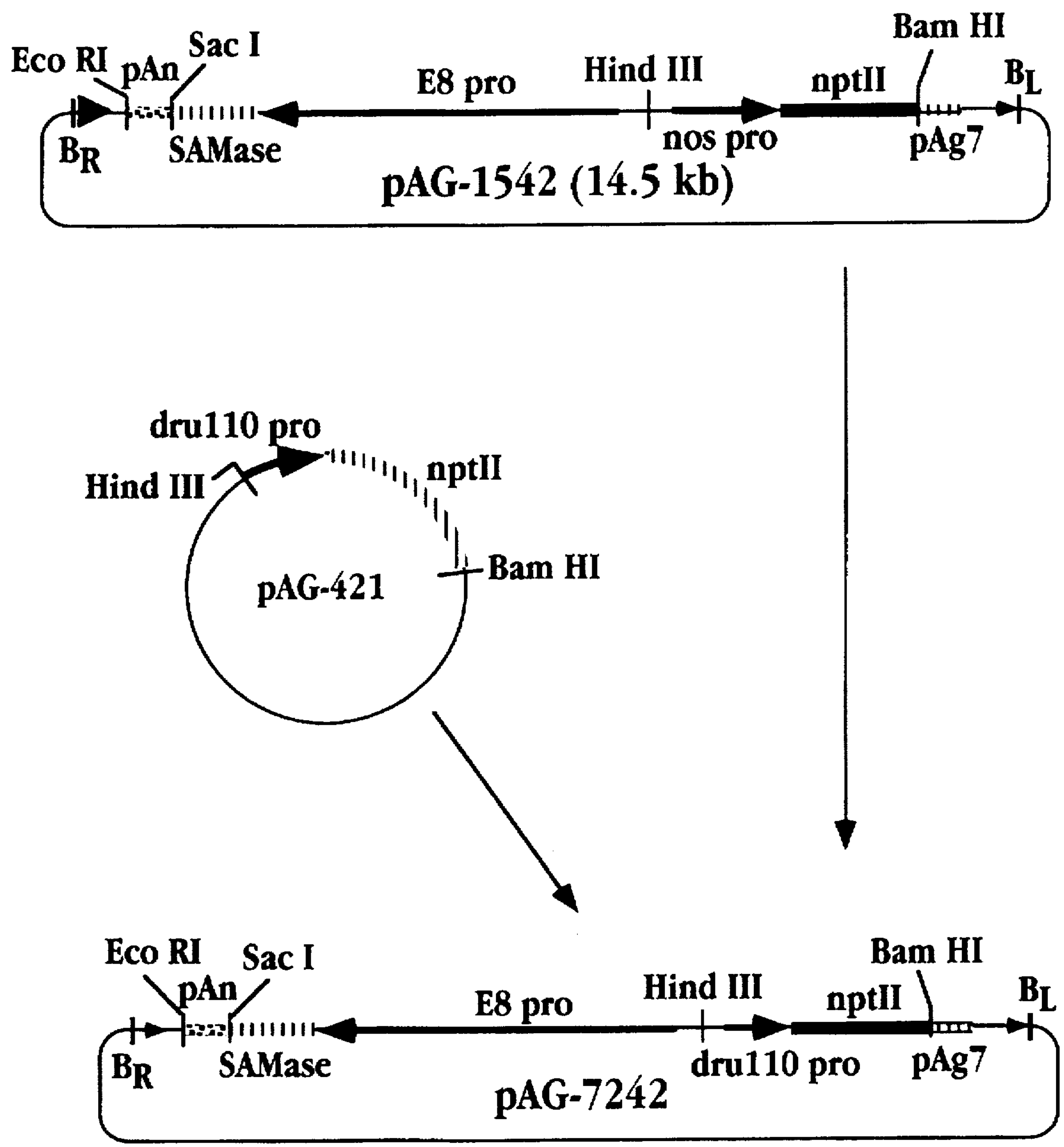
FIG. 3 outlines the steps involved in the construction of Agrobacterium binary vector pAG-7242, containing drullo pro fused to the nptII gene, from plasmids pAG-1542 and pAG-421.
Figure 4:
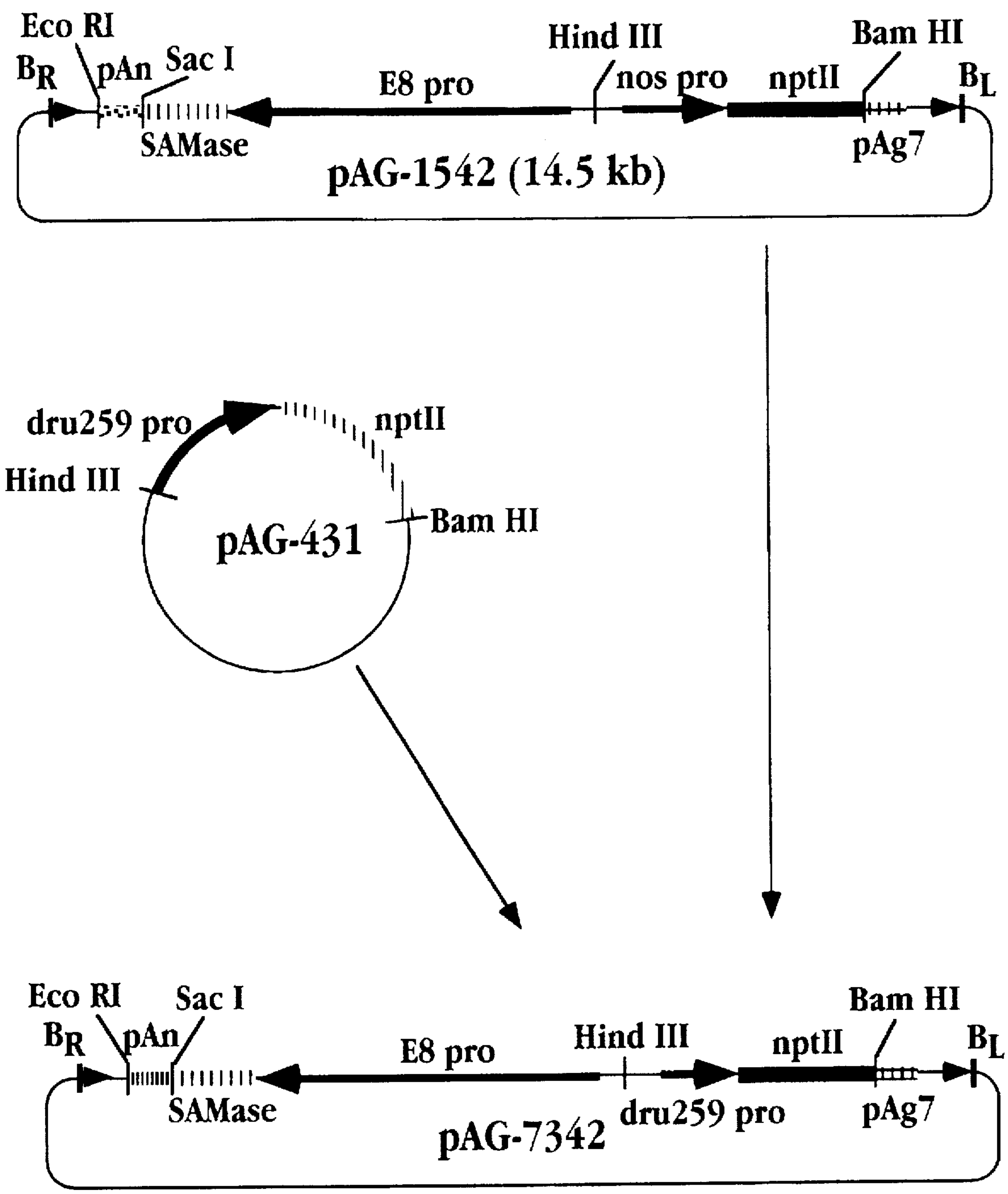
FIG. 4 is a flow chart depicting the creation of Agrobacterium binary vector pAG-7342 containing a chimeric dru259 pro-nptII gene.

Construction of Agrobacterium binary vectors, pAG-7242 and pAG-7342, containing the two representative chimeric genes described above, can be performed as described in Example 10 and Example 19 (schematically represented in FIGS. 3–4, dru110pro:nptII, and dru259pro:nptII, respectively). These binary vectors also contain a gene encoding SAMase, S-adenosylmethionine hydrolase (Ferro, et al., 1995; Hughes, et al., 1987), which is immaterial to the present invention.

1. Construction of a Binary Plant Transformation Vector pAG-7342 Containing a dru259::nptII Chimeric Gene. Binary plant transformation vector, pAG-7342, is constructed by excising a 13 kb nos pro::nptII fragment from subclone pAG-1542 by digestion with HindIII and BamHI, followed by ligation to a 1.1 kb HindIII-BamHI fragment from subcloning vector, pAG-431, to insert a dru259 pro::nptII chimeric gene.

Plasmid pAG-1542 can be prepared using conventional cloning techniques known in the art (Sambrook, et al., 1989). This illustrative subcloning binary vector contains a neomycin phosphotransferase II selectable marker gene (nptII) gene under the control of the nos promoter located near the left border, and the SAMase gene (Ferro, et al., 1995) driven by the tomato E8 promoter (Deikman, et al., 1988; Deikman, et al., 1992) located near the right border. As previously stated, the presence of the tomato E8:SAMase construct is immaterial to the expression results described herein.

Construction of subclone pAG-431, containing the dru259::nptII chimeric gene, is described in Example 7. Construction of binary plant transformation vector pAG-7342 is depicted schematically in FIG. 4 and detailed in Example 9.

Figure 17A:
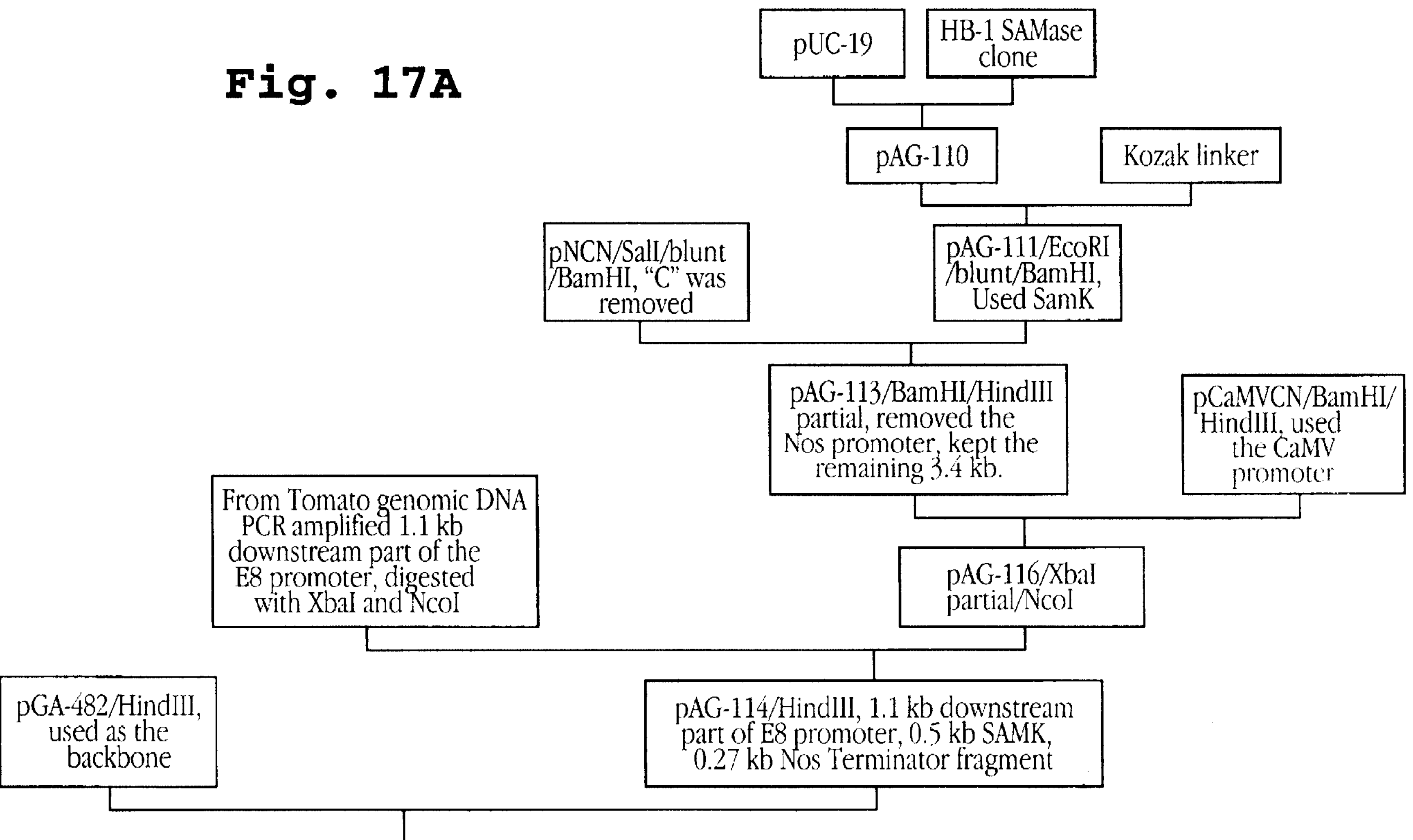
FIGS. 17A and 17B depict a flow chart summarizing the construction of plasmid pAG-1542.
Figure 17B:
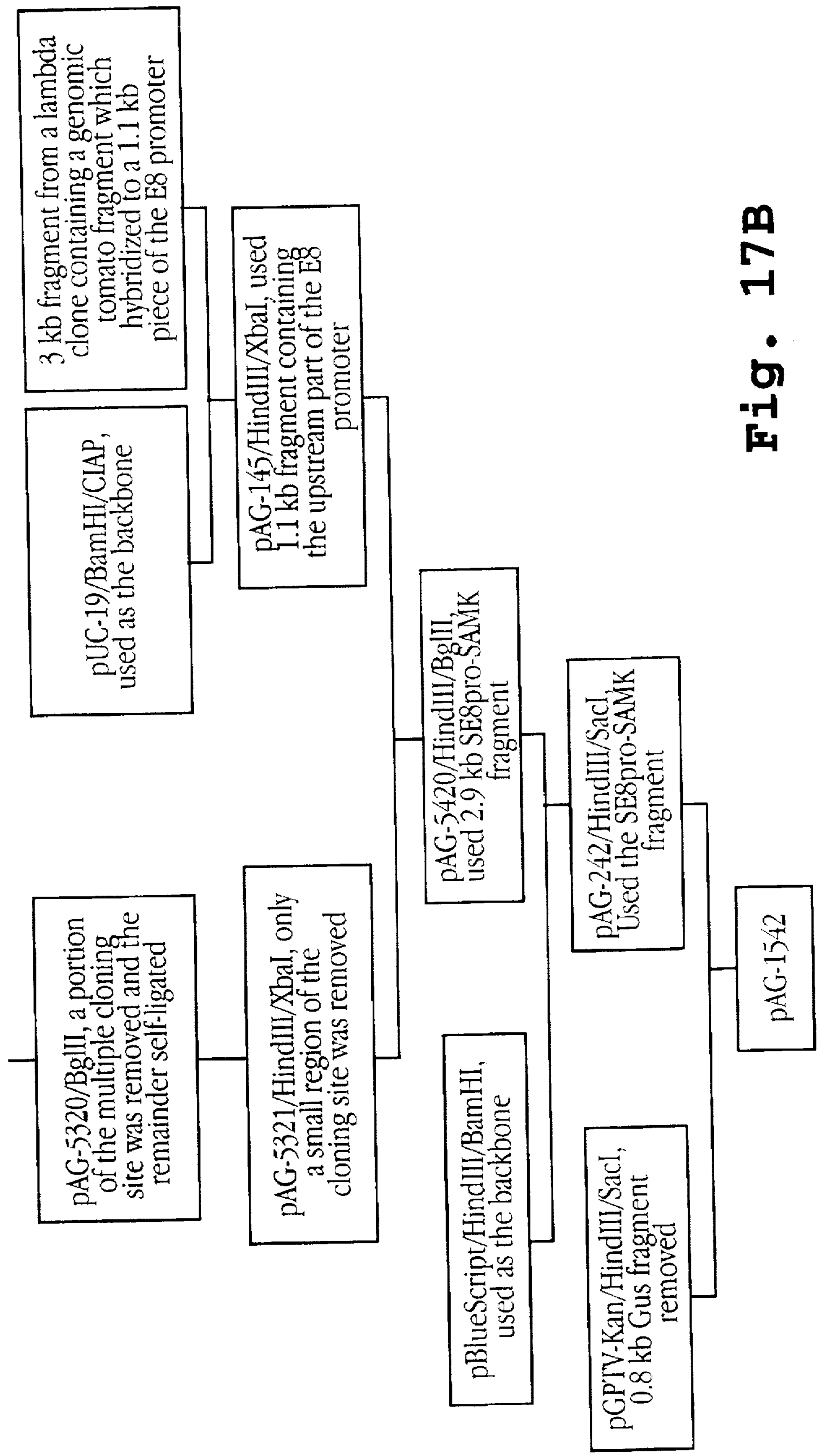

A flow chart summarizing the construction of plasmid pAG-1542 is presented in FIG. 17.

2. Construction of a Binary Plant Transformation Vector Containing a dru110::nptII Chimeric Gene. Utilizing a similar approach, binary plant transformation vector, pAG-7242, is constructed by excising a 13 kb nos pro::nptII fragment from subclone pAG-1542 by digestion with HindIII and BamHI, followed by ligation to a 0.95 kb dru259::nptII fragment from pAG-421 to form the binary plant transformation vector pAG-7242.

Construction of binary plant transformation vector pAG-7242 is depicted schematically in FIG. 3 and described in Example 10. Construction of subclone pAG-421, containing the dru110::nptII chimeric gene, is described in Example 8.

B. Methods of Transforming Plants

The above-described chimeric genes can be inserted, for example, into plant cells. Transgenic plants containing these exemplary chimeric genes, regulated by the raspberry promoters of the invention, express neomycin phosphotransferase II, which confers to plants expressing the product, resistance to the antibiotic, kanamycin.

In experiments performed in support of the invention, the chimeric genes were inserted into tomato plant cells, and the resulting levels and patterns of expression of the nptII selectable marker gene were examined. Although nptII was selected as an exemplary marker gene to illustrate the ability of a raspberry plant promoter of the invention to regulate expression of a gene under its control, it will be understood that expression of any of a number of heterologous genes can be directed by the promoters of the present invention.

For example, nptI and nptII are different and distinct enzymes, with differences in both their amino acid sequences and substrate specificities (Beck, et al., 1982). The raspberry promoters of the invention are suitable for directing expression of either of these neomycin phosphotransferases.

Plants suitable for transformation using the raspberry promoters of the invention include but are not limited to, raspberry, tomato, strawberry, banana, kiwi fruit, avocado, melon, mango, papaya, apple, peach, soybean, cotton, alfalfa, oilseed rape, flax, sugar beet, sunflower, potato, tobacco, maize, wheat, rice, and lettuce.

Chimeric genes containing a raspberry promoter, e.g., dru110, and dru259, can be transferred to plant cells by any of a number of plant transformation methodologies. One such method, employed herein, involves the insertion of a chimeric gene into a T-DNA-less Ti plasmid carried by *A. tumefaciens*, followed by co-cultivation of the *A. tumefaciens cells* with plant cells.

As provided in Example 11, Agrobacterium binary plant transformation vectors, pAG-7242 and pAG-7342, are individually introduced into a disarmed strain of *A. tumefaciens* by electroporation (Nagel, et al., 1990), followed by co-cultivation with tomato plant cells, to transfer the chimeric genes into tomato plant cells.

In addition to Agrobacterium-based methods, alternative methodologies may be employed to elicit transformation of a plant host, such as leaf disk-based transformation, electroporation, microinjection, and microprojectile bombardment (particle gun transformation). These methods are well known in the art (Fry, et al., 1987; Comai and Coning, 1993; Klein, et al., 1988; Miki, et al., 1987; Bellini, et al., 1989) and provide the means to introduce selected DNA into plant genomes. Such DNA may include a DNA cassette which consists of a raspberry promoter (e.g., dru110, dru259) functionally adjacent a heterologous coding sequence.

Additionally, an iterative culture-selection methodology may be employed to generate plant transformants, and is particularly suited for transformation of woody species, such as raspberry. This method is described in detail in co-owned U.S. patent application Ser. No. 08/263,900, filed on 17 Jun. 1994, and entitled "Plant Genetic Transformation Methods and Transgenic Plants", and in co-owned U.S. patent application Ser. No. 08/384,556, filed on 03 Feb. 1995, also entitled "Plant Genetic Transformation Methods and Transgenic Plants". The contents of both of these applications are herein incorporated by reference.

In employing an iterative culture-selection transformation methodology, a chimeric gene of interest is inserted into cells of a target plant tissue explant, such as by co-culturing a target explant in the presence of Agrobacterium containing the vector of interest. Typically, the co-culturing is carried out in liquid for from about 1 to about 3 days. The plant tissue explant can be obtained from a variety of plant tissues including, but not limited to, leaf, cotyledon, petiole and meristem.

Transformed explant cells are then screened for their ability to be cultured in selective media having a threshold concentration of selective agent. Explants that can grow on the selective media are typically transferred to a fresh supply of the same media and cultured again. The explants are then cultured under regeneration conditions to produce regenerated plant shoots. These regenerated shoots are used to generate explants. These explants from selected, regenerated plant shoots are then cultured on a higher concentration of selective agent. This iterative culture method is repeated until essentially pure transgenic explants are obtained.

Pure transgenic explants are identified by dividing the regenerated plant shoots into explants, culturing the explants, and verifying that the growth of all explants is resistant to the highest concentration of selective agent used. That is, in the presence of selective agent there is no necrosis or significant bleaching of the explant tissue. Upon confirmation of production essentially pure transgenic explants, transgenic plants are produced by regenerating plants from the pure transgenic explants.

C. Identification and Evaluation of Plant Transformants

Transgenic plants are assayed for their ability to synthesize product mRNA, DNA, protein, and/or for their resistance to an aminoglycoside antibiotic, e.g., kanamycin. The assays are typically conducted using various plant tissue sources, e.g., leaves, stem, or fruit.

Leaf-based assays are informative if the raspberry promoter driving the heterologous gene (transgene) is at least somewhat active in leaf tissue, as is the case for exemplary promoters dru110 and dru259. In such cases, leaf-based assays are useful for initial screens of the expression level of a transgene, since they can be performed much earlier than fruit-based assays. Fruit-based assays, on the other hand, provide more accurate data on transgene expression in a target tissue itself such as fruit.

RNA-based assays can be carried out using, for example, an RNAase protection assay (RPA). In carrying out such an assay, mRNA is typically extracted from plant cells derived from both transformed plants and wild-type plants. RNAse Protection Assays (RPA) can be performed according to the manufacturer's instructions using an "RPAII" kit from Ambion, Inc. (Hialeah, Fla.), as previously described by Lee, et al., 1987.

Gene expression patterns for transgenic plants containing chimeric genes regulated by a raspberry promoter can also be evaluated by conducting Northern dot blots (e.g., Example 6). Promoter function (i.e., tissue and/or stage specific expression, or constitutive expression) can be evaluated by comparing northern blots of total RNA from leaf and fruit tissues at different ripening stages to northern blots of total RNA from various other plant tissues.

Experiments carried out in support of the invention indicate that the raspberry promoters, dru110 and dru259, do not function as stage or tissue-specific promoters. This is somewhat surprising, since a tissue and stage specific gene expression pattern of dru1, regulated by the full length dru1 promoter, was confirmed on northern blots of total RNA from leaf, receptacles, and drupelets.

As a further confirmation of expression of a downstream heterologous gene regulated by a raspberry promoter of the invention, a Western blot analysis can be carried out. In conducting a typical Western blot experiment, total soluble protein is extracted from frozen plant tissue and measured using, for example, the Coomassie Plus protein assay (Pierce, Rockford, Ill.). Known quantities of soluble protein, or known quantities of purified protein product (e.g., neomycinphosphotransferase II, positive control) are resolved on a polyacrylamide gel and transferred to nylon membranes. The bound proteins were then probed with a monoclonal antibody specifically immunoreactive with the protein product.

In another approach for confirming gene expression directed by raspberry promoter of the invention, a Southern hybridization analysis is performed. Typically, plant DNA is extracted by grinding frozen plant tissue in extraction buffer, followed by centrifugation, separation of the resulting supernatant, and precipitation with cesium chloride. The resulting CsCl gradients are then centrifuged for an extended period of time (e.g., 48 h), and the recovered DNA is dialyzed and precipitated with ethanol. Upon recovery of plant DNA, the DNA is digested with suitable restriction enzymes to obtain DNA fragments, followed by electrophoretic separation on agarose gel. The resulting bands are transferred to nitrocellulose (Southern, 1975), and the blots are then probed with a labelled DNA fragment containing the nucleotide sequence of the transgene, to confirm the presence of DNA corresponding to a raspberry promoter-chimeric gene construct, as described above.

D. Comparative Evaluation of Gene Expression and Promoter Strength

Experiments performed in support of the invention demonstrate the transformation of tomato plants with chimeric genes operably linked to a raspberry promoter of the present invention (e.g., dru110, dru259). As is evident from the results of these experiments, the raspberry promoters of the invention are capable of regulating expression of genes placed under their control, and function as moderate level, constitutive promoters.

Tomato plants were transformed with plant transformation vectors, pAG-7242 and pAG-7342, each containing a raspberry promoter operably linked to an nptII gene (Example 11). As detailed in sections V.A.1–2 above, plant transformation vector pAG-7242 contains the dru110::nptII gene; and construct pAG-7342 contains the dru259::nptII gene. Chimeric genes containing either the hsp80 promoter or the CAS promoter (caulimovirus cassava mottle vein virus promoter) fused to the nptII gene were also prepared and used to transform tomato plants, to provide a comparative basis for evaluating performance of the raspberry promoters of the invention.

Results from ten separate transgenic events employing the constructs described above are provided in Example 12. To detect the presence of nptII enzymatic activity in plant transformants, protein extracts from leaf tissue of rooted plants available at the time of culture were assayed by ELISA. In some cases, only 1 plant was available for assay (e.g., Table 1, last two rows, column IV), while in other instances (e.g., Table 1, row 2, column IV), ten separate transgenic events were available for analysis.

In referring now to transgenic plants containing a raspberry promoter of the invention (e.g., dru110, dru259), as can be seen from the results in Table 1 (specifically, rows 3–7), nptII enzymatic activity was detected in a high percentage of the plants assayed, with values ranging from about 20–100%, depending upon the concentration of selection agent used and the number of rooted plants tested. These results are comparable to those obtained for transgenic plants containing known promoter::nptII constructs, and indicate that the raspberry promoters of the invention are effective to regulate expression of heterologous genes placed under their control.

Also provided in Table 1 is a comparison of transformation frequency, that is, the ratio of the number of tissue explants producing regenerated shoots that are capable of rooting in the presence of selection agent to the total number of initial explants, expressed as a percentage. Based on the results in column III, and referring to plants containing a raspberry promoter of the invention, on average, at least about half of the plants transformed with a raspberry promoter-containing construct survived selection with antibiotic, that is, they were capable of rooting in the presence of an amount of selection agent that would otherwise be toxic to non-transformed plant cells.

As in the case of the neomycin phosphotransferase assay discussed above, these results are consistent with those obtained with known plant promoters (hsp80, CAS), and further illustrate (i) the capability of the raspberry promoters of the invention to regulate expression of genes placed under their control, and (ii) the formation and use of chimeric gene constructs and transformation vectors containing a raspberry promoter (dru110, dru259), for transforming a plant host to form a transgenic plant expressing a heterologous gene.

The raspberry promoters of the invention provide constitutive expression of heterologous genes, as evidenced by the detection of nptII activity in all tissues obtained from transgenic plants transformed with exemplary plant transformation vectors pAG-7242 and pAG-7342.

Promoter-driven expression of the nptII gene was evaluated by determining nptII enzyme levels in transformants. The results are presented in Table 2 and in FIG. 5. Protein levels for leaf tissue obtained from transformants containing the CAS::nptII chimeric gene are not included in either the table or the figure, since values from two CAS::nptII events assayed were in excess of 6000 pg/ml, indicating the high level of gene expression regulated by the CAS promoter (i.e., a strong promoter). While the dru1 promoters of the invention appear to direct transgene expression at levels somewhat lower than those observed for the hsp80 promoter, both dru110 and dru259 are considered to function as moderate-level promoters.

In looking at the results for the first two transgenic events in Table 2, the average nptII enzyme level for dru110 (dru259): :nptII plants was about 5–9% that determined for CAS::nptII plants.

In examining these same results, using the hsp80 promoter as a basis for comparison, the average nptII enzyme activity determined for dru110 (dru259)::nptII plants was about 40–60% of the nptII enzyme activity determined for hsp80::nptII plants.

Thus, promoters derived from the dru1 gene, e.g., dru110 and dru259, provide somewhat lower levels of gene expression than the hsp80 promoter, but are also considered to function as moderate strength promoters. As supported by the data described above, each of the exemplary raspberry promoters described herein is capable of directing constitutive expression of a transgene at sufficient levels to support its use in regulating expression of any of a number of heterologous gene products.

Additionally, the transformation of tomato plants using the raspberry promoters of the present invention illustrates that a promoter region derived from raspberry can be used to promote expression of a gene within plant cells from a completely different genus, family, or species of plant.

VI. Vectors of the Present Invention

The present invention provides vectors suitable for the transformation of plants. The vectors, chimeric genes and DNA constructs of the present invention are also useful for the expression of heterologous genes. Transgenic plants carrying the chimeric genes of the present invention may be a useful source of recombinantly-expressed material.

In one embodiment, the chimeric genes of the present invention have two components: (i) a constitutive promoter derived from a raspberry dru1 gene, and (ii) a heterologous DNA sequence encoding a desirable product.

The vectors of the present invention may be constructed to carry an expression cassette containing an insertion site for DNA coding sequences of interest. The transcription of such inserted DNA is then under the control of a suitable raspberry promoter (e.g., dru110pro or dru259pro) of the present invention.

Such expression cassettes may have single or multiple transcription termination signals at the coding-3'-end of the DNA sequence being expressed. The expression cassette may also include, for example, DNA sequences encoding (i) a leader sequence (e.g., to allow secretion or vacuolar targeting), and (ii) translation termination signals.

Further, the vectors of the present invention may include selectable markers for use in plant cells (such as, a neomycin phosphotransferase II gene (nptII) or a neomycin phosphotransferase I gene). The presence of the nptII gene confers resistance to the antibiotic, kanamycin. Another aminoglycoside resistance gene for use in vectors of the invention includes a gene encoding hygromycin phosphotransferase, i.e., an hpt gene (Gritz, et al., 1983). Plant cells containing the hpt gene are able to grow in the presence of the aminocyclitol antibiotic, hygromycin B. Other selectable marker sequences for use in the present invention include glyphosate-tolerant CP4 and COX genes (Zhou, et al., 1995). Transgenic plants expressing either of these genes exhibit tolerance to glyphosate, which can be used in selection media to select for plant transformants.

The vectors may also include sequences that allow their selection and propagation in a secondary host, such as, sequences containing an origin of replication and a selectable marker. Typical secondary hosts include bacteria and yeast. In one embodiment, the secondary host is *Escherichia coli*, the origin of replication is a colEl-type, and the selectable marker is a gene encoding ampicillin resistance. Such sequences are well known in the art and are also commercially available (e.g., Clontech, Palo Alto, Calif.; Stratagene, La Jolla, Calif.).

The vectors of the present invention may also be modified to intermediate plant transformation plasmids that contain a region of homology to an *Agrobacterium tumefaciens* vector, a T-DNA border region from *Agrobacterium tumefaciens*, and chimeric genes or expression cassettes (described above). Further, the vectors of the invention may comprise a disarmed plant tumor inducing plasmid of *Agrobacterium tumefaciens.*

The vectors of the present invention are useful for moderate level constitutive expression of nucleic acid coding sequences in plant cells. For example, a selected peptide or polypeptide coding sequence can be inserted in an expression cassette of a vector of the present invention. The vector is then transformed into host cells, the host cells are cultured under conditions to allow the expression of the protein coding sequences, and the expressed peptide or polypeptide is isolated from the cells. Transformed progenitor cells can also be used to produce transgenic plants bearing fruit.

The vectors, chimeric genes and DNA constructs of the present invention can be sold individually or in kits for use in plant cell transformation and the subsequent generation of transgenic plants.

A. Heterologous Genes

The methods and results described herein demonstrate the ability of the raspberry promoters of the invention to provide constitutive, moderate level gene expression in transgenic plants. A raspberry promoter of the present invention includes a region of DNA that promotes transcription of the immediately adjacent (downstream) gene constitutively, in numerous plant tissues. According to methods of the present invention, heterologous genes are operably linked to a raspberry promoter of the present invention.

Exemplary heterologous genes for the transformation of plants include genes whose products are effective to confer antibiotic resistance. Some of these genes, including the nptII gene, are described above.

Other genes of interest that can be used in conjunction with a raspberry promoter of the invention (e.g., dru110, dru259) include, but are not limited to, the following: genes capable of conferring fungal resistance, such as the polygalacturonase inhibiting protein (PGIP) gene from *Phaseolus vulgaris* (Toubart, et al., 1992) and modified forms of plant glucanase, chitinase (Jongedijk, et al., 1995) and other pathogenesis related (PR) genes (Melchers, et al., 1994; Ponstein, et al., 1994; Woloshuk, et al., 1991). These gene products (e.g., chitinases or β-1,3-glucanases) 41 can, for example, enhance resistance to fungi such as Fusarium, *Sclerotinia sclerotiorum*, and *Rhizoctonia solani*. Transformed plants expressing these products exhibit increased resistance to diseases such as seedling damping off, root rot disease, and the like. Other representative genes for conferring both viral and fugal resistance to transgenic plants are described in "VIRUS AND FUNGAL RESISTANCE: FROM LABORATORY TO FIELD" (Van Den Elzen, et al., 1994).

Additional exemplary heterologous genes for use with a raspberry promoter of the present invention include genes whose products are effective to confer herbicide-resistance to transformed plant cells. Exemplary herbicide resistance genes include a bialaphos resistance gene (bar) which codes for phosphinothricin acetyltransferase (PAT) (Akama, et al., 1995). Transgenic plants containing this gene exhibit tolerance to the herbicide, "BASTA". This gene can also be used as a selectable marker gene, since explants carrying the bar gene are capable of growing on selective media containing phosphinothricin (PPT), which is an active component of bialaphos.

Additional herbicide resistance genes include those conferring resistance to glyphosate-containing herbicides. Glyphosate refers to N-phosphonomethyl glycine, in either its acidic or anionic forms. Herbicides containing this active ingredient include "ROUNDUP" and "GLEAN". Exemplary genes for imparting glyphosate resistance include an EPSP synthase gene (5-enolpyruvyl-3-phosphosshikimate synthase) (Delanney, et al., 1995; Tinius, et al., 1995), or an acetolactate synthase gene (Yao, et al., 1995).

Other exemplary DNA coding sequences include a bxn gene encoding a bromoxynil-specific nitrilase (Stalker, et al., 1988), under the transcriptional control of a dru1 promoter. Transformed plants containing this chimeric gene express a bromoxynil-specific nitrilase and are resistant to the application of bromoxynil-containing herbicides.

Other gene products which may be useful to express using the promoters of the present invention include genes encoding a viral coat protein, to enhance coatprotein mediated virus-resistance in transgenic plants. Exemplary genes include genes coding for alfalfa mosaic virus coat protein (AlMV), cucumber mosaic virus coat protein (CMV), tobacco streak virus coat protein (TSV), potato virus coat protein (PVY), tobacco rattle virus coat protein (TRV), and tobacco mosaic virus coat protein (TMV) (Beachy, et al., 1990). Thus, a chimeric 15 gene of the invention will contain a viral coat protein gene, such as an ALMV, CMV, TSV, PVX, TRV, or TMV gene, under the transcriptional control of a raspberry a dru1 promoter.

B. Expression in Heterologous Plant Systems

Experiments performed in support of the present invention demonstrate the versatility of the chimeric gene constructs of the invention. The vector constructs of the present invention can be used for trans formation and expression of heterologous sequences in transgenic plants independent of the original plant source for the promoter sequence. For example, the dru110::nptII and dru259::nptII chimeric genes were successfully introduced into tomato plant cells.

These data suggest that the raspberry promoters of the invention (e.g., dru110, dru259) are useful for promoting gene expression in heterologous plant systems, i.e., plant cells other than raspberry, such as tomato. Further, the expression mediated by the promoters appears to be constitutive even in heterologous plants. These findings support the usefulness of the vectors, chimeric genes and DNA constructs of the present invention for transformation of plants.

VII. Utility

Experiments performed in support of the present invention demonstrate that the gene expression patterns of nptII directed by a dru1 promoter, such as dru110 or dru259, are observed in various plant tissues (e.g., leaf, stem, fruit, root). Accordingly, use of a raspberry promoter of the invention allows constitutive expression of a foreign gene placed under its control.

The raspberry dru1-derived promoters of the invention, dru110 and dru259, can be cloned as described above employing sequence information described herein. These raspberry promoters can be used to express any heterologous gene whose function would be enhanced or enabled by a moderate level, constitutive promoter. Exemplary genes are described above.

The use of these promoters cannot be considered limited to raspberries, particularly in view of the successful transformation of tomato using the raspberry promoters of the invention. Since raspberry is essentially a miniature drupe fruit, it is likely that the raspberry promoters will function in other drupe fruits. The constructs and methods of the present invention are applicable to all higher plants including, but not limited to, the following: Berry-like fruits, for example, Vitis (grapes), Fragaria (strawberries), Rubus (raspberries, blackberries, loganberries), Ribes (currants and gooseberries), Vaccinium, (blueberries, bilberries, whortleberries, cranberries), Actinida (kiwifruit and Chinese gooseberry). Further, other drupe fruits, including, but not limited to, Malus (apple), Pyrus (pears), most members of the Prunus genera, sapota, mango, avocado, apricot, peaches, cherries, plums, and nectarines. Additional plant sources are described above.

The present invention provides compositions and methods to regulate plant cell expression of any gene in a constitutive manner. In one embodiment, the promoters of the present invention can be used to regulate expression of a selectable marker gene, such as nptII. Alternatively, the raspberry promoters can be used to promote expression of a herbicide-resistance gene, or to regulate expression of a gene encoding a viral coat protein, to provide enhanced virus resistance.

The raspberry promoters of the invention can be used in chimeric genes, plant transformation vectors, expression cassettes, kits, and the like, to promote transformation of plant cells.

The raspberry promoters described herein may also be employed in a method for providing moderate level expression of a heterologous gene, such as a selectable marker gene, in a transgenic plant.

The following examples illustrate, but in no way are intended to limit the scope of the present invention.

MATERIALS AND METHODS

Biological reagents were typically obtained from the following vendors: 5' to 3' Prime, Boulder, Co.; New England Biolabs, Beverly, Mass.; Gibco/BRL, Gaithersburg, MD; Promega, Madison, Wis.; Clontech, Palo Alto, Cailf.; and Operon, Alameda, Calif. Standard recombinant DNA techniques were employed in all constructions (Adams and Yang, 1977; Ausubel, et al., 1992; Hooykaas and Schilperoot 1985; Sambrook, et al., 1989; Wang, et al., 1990; Kawasaki, et al., 1989; Veluthambi, et al., 1988; Benvenuto, et al., 1988).

EXAMPLE 1

Raspberry Drupelet Protein Characterization and Purification

A. Protein Lysate Preparation and Gel Electrophoresis

Using a mortar and pestle containing liquid nitrogen, a raspberry protein sample was prepared by grinding the frozen drupes of one whole berry into a fine powder. Sample buffer (0.05M Tris, pH 6.8, 1% SDS, 5% β-mercaptoethanol, 10% glycerol; Laemelli, 1970) was added (900 μls) to the tissue and the sample mixed by vortexing. The sample was heated for 10 minutes at 90°–95° C. and centrifuged at 14K rpm, 4° C. for 10 minutes. The supernatant was removed from the insoluble debris pellet and stored at −20° C.

Drupelet proteins were analyzed by sodium dodecyl sulfate polyacrylamide gel electrophoresis (SDS PAGE) combined with coomassie blue staining using standard procedures. A coomassie blue-stained SDS polyacrylamide gel of soluble drupelet proteins is shown in FIG. 10. In the figure: lane 1, molecular weight markers (BioRad, Richmond, Calif.), lanes 2, 3 and 5 each contain 9 μg of raspberry drupelet protein lysate prepared separately from individual fruit. Lane 4 contained a higher amount of lysate.

Two highly abundant proteins were observed at approximately 17 and 15 kd and were named drupe1 and drupe2, respectively. In FIG. 10 these two proteins are indicated by arrows. Scanning densitometry analysis of this gel indicated drupe1 and drupe2 comprise approximately 23 and 37%, respectively, of the total soluble protein in raspberry drupelets. As a result, a direct western blot approach to purification and sequencing of the protein was followed.

B. Protein Blot For Sequencing

A protein blot (Applied Biosystems, Inc. User Bulletin Number 58; Ausubel, et al., 1992) was prepared using the raspberry protein lysate described above. Varying amounts of raspberry protein lysate (12–36 μg/well) were loaded on a 10 well 18% SDS-PAGE minigel (1.5 mm thick) with 4.5% stacker and electrophoresed at 100 volts in 25 mM Tris, 192 mM glycine, 0.1% SDS buffer for 2–2.5 hours.

Proteins were transblotted onto Applied BioSystem's "PROBLOTT" polyvinylidene difluoride (PVDF) membrane in a 25 mM Tris, 192 mM glycine, 10% methanol buffer at 90 volts for 2 hours at 4° C. After protein transfer, the blot was Coomassie blue stained and the and 17 kilodalton (kd) protein bands were located on the blot and cut out. N-terminal sequencing of the proteins was carried out at the W. M. Reck Foundation, Biotechnology Resource Laboratory in New Haven, Conn.

The drupe1 sample yielded a thirty amino acid N-terminal sequence. The drupe2 sample did not yield useful sequence information likely due to a blocked amino terminus. The amino terminal drupe1 sequence is presented as SEQ ID NO:11. This 30 amino acid drupe1 sequence was compared to the protein database using BLAST searching; no significant matches were found indicating that drupe1 is a novel protein.

EXAMPLE 2

Recovering a cDNA Clone Corresponding to the Drupe1 Protein

A. Drupelet Total RNA Preparation

RNA was extracted from mature green raspberry drupelets. Four mature green raspberry fruit, which had been picked in season and stored at −80° C., were used to extract RNA. The estimated weight of the drupelets was 12 grams. In a cold mortar, which contained liquid nitrogen, the whole berries were fractured by tapping them with a pestle. The drupelets were separated from the receptacles. The receptacles were removed from the mortar and discarded. The drupelets were ground to a powder in the mortar, adding liquid nitrogen as necessary to keep the tissue frozen. The seeds were purposefully left intact. Homogenization buffer, 2 ml/gram of tissue, was used to extract the RNA. [Homogenization buffer: 200 mM Tris-HCl pH 8.5, 300 mM LiCl, 10 mM $Na_2EDTA$, 1% (w/v) sodium deoxycholate, 1.5% (w/v) sodium dodecyl sulfate (SDS), 8.5% (w/v) insoluble polyvinylpolypyrollidone (PVPP), 1% (v/v) NP-40, 1 mM aurintricarboxylic acid (ATA), 5 mM thiourea, and 10 mM dithiothreitol (DTT); the last three components were added after autoclaving].

The frozen powdered drupelet tissue was added to the buffer in 3 to 5 portions, vortexing between additions until all tissue was moistened. The tissue plus buffer solution (referred to herein as the pulp) was diluted 1:1 with sterile water and 0.75 volumes of homogenization buffer were added to the diluted pulp. The sample was incubated at 65° C. for 10 to 15 minutes, followed by centrifugation in a swinging bucket rotor at 9000 g for 15 minutes at 4° C. The supernatant was transferred to a clean tube. Cesium chloride (CsCl) was added to the supernatant at 0.2 g/ml. The sample was mixed until the CsCl dissolved.

A 4 ml cushion was dispensed into a Beckman 1×3.5 inch polyallomer ultracentrifuge tube (cushion: 5.7M CsCl, 10 mM Tris-HC1, pH 8.0, 1 mM $Na_2EDTA$, pH 8.). The sample was gently layered on top of the cushion. The sample was spun in a Beckman L8–80M ultracentrifuge with a SW 28 rotor at 23,000 rpm at 20° C. for 20 hours. After removing the sample from the ultracentrifuge the supernatant was pulled off the sample by using a drawn Pasteur pipette attached to an aspirator. A clear lens-like pellet was visible in the bottom of the tube.

The pellet was dissolved in 500 µl SSTE and transferred to a microfuge tube (SSTE: 0.8M NaCl, 0.4% SDS, 10 mM Tris-HC1, pH 8.0 and 1 mM $Na_2EDTA$, pH 8). The sample was extracted twice with an equal volume of chloroform:i-soamyl alcohol (24:1). To precipitate the RNA, 2.5 volumes ethanol were added to the aqueous phase. The sample was collected by centrifugation, washed two times with 75% ethanol and resuspended in 100 µl TE. The yield was 1.6 mg. The RNA was reprecipitated with ⅒ volume 3M sodium acetate and 3 volumes ethanol for storage at −20° C.

B. Drupelet mRNA Preparation

The isolation of mRNA from mature green raspberry drupelet total RNA was performed using the "STRAIGHT A'S" mRNA isolation system (Novagen, Madison, WI) according to the manufacturer's instructions. mRNA was isolated from the 1.6 mg of total RNA extracted from mature green raspberry drupelets described above. The yield of mRNA from this procedure was 6.6 µg.

C. Preparation of cDNA From Green Raspberry Drupelet mRNA

The mRNA from mature green raspberry drupelet RNA was used as the template for cDNA synthesis. The primer for the cDNA reactions was dTRANDOM (SEQ ID NO:12; synthesized by Operon Technologies, Inc., Alameda, Calif.). The oligo(dT) region hybridized to the poly(A) region (corresponding to SEQ ID NO:21, as shown in the top portion of FIG. 11A) of the mRNA pool. The other 15 nucleotides created a 5' overhang that was used to facilitate PCR amplification at a later step in the cloning process.

The following reaction mixture was assembled for the cDNA synthesis reaction: $H_2O$, 10.2 µl; 250 ng mRNA, 0.8 µl; 5×BRL RT buffer (BRL, Bethesda, Md.), 4.0 µl; 100 mM DTT (dithiothreitol-BRL, Bethesda, Md.), 0.2 µl; "RNAI-GUARD" (23.4 U/µl; an RNase inhibitor from Pharmacia, Piscataway, N.J.), 0.5 µl; dNTP's (2.5 mM each), 2.0 µl; 50 µM primer, 1.0 µl; [$^{32}$P]dCTP (3000 Ci/mmol; DuPont/NEN, Boston, Mass.), 1.0 µl; and AMV reverse-transcriptase (38 U/µl; Life Sciences, Inc., St. Petersburg, Fla.), 0.3 µl. The cDNA reaction was performed by combining mRNA and water for the reaction and heating to 65° C. for 3 minutes. The mixture was cooled on ice and microfuged (to collect condensation). The remaining reaction components were then added.

After incubating at 42° C. for 1 hour the cDNA reactions were moved to ice and stored at 4° C. prior to their use in PCR reactions. The preparation of cDNA from mRNA is illustrated in the top portion of FIG. 11A. A portion of the 3' end of the first cDNA strand is shown in the second set of reactions in FIG. 11A, the sequence of which is presented herein as SEQ ID NO:22.

EXAMPLE 3

PCR Amplification and Cloning of the cDNA dru1 Fragment

A degenerate PCR primer, Drupe20, was designed for the 5' end of the cDNA based on the reverse translation of the dru1 protein sequence. A section of the known amino acid sequence of dru1 (SEQ ID NO:13) was chosen for its proximity to the amino terminus and for the relatively low level of degeneracy in its reverse—translated sequence (SEQ ID NO:14; Drupe20). The Drupe20 primer (i) is the 512-fold degenerate nucleotide sequence corresponding to the amino acid sequence presented as SEQ ID NO:13, and (ii) was used as the 3'-primer. The product from the first round of PCR amplification is illustrated in FIG. 11A (second set of reactions), where a portion of the sequence at the 3' end of the product corresponds to SEQ ID NO:23 (which is also the complement of SEQ ID NO:12).

The 5' PCR primer (DrupeRAN18, SEQ ID NO:15, corresponding to the cDNA primer, dTRANDOM) was designed for the 3' end. The product from the second round of PCR amplification is shown in FIG. 11A (third set of reactions), where a portion of the sequence corresponding to the 3' end of the product is presented herein as SEQ ID NO:24 (which is also the complement of SEQ ID NO:14). Polymerase chain reaction (PCR; Perkin-Elmer Cetus, Norwalk, Conn.; Mullis, 1987; Mullis, et al., 1987, was performed following the manufacturer's procedure using "AMPLITAQ" (Perkin Elmer Cetus), PCR buffer II (50.0 mM KCl, 10 mM Tris-HCl, pH 8.3), 2 mM $MgCl_2$, 0.2 mM of each dNTP, mature green drupelet cDNA and Drupe20 and DrupeRAN18 primers under the following conditions:

1 cycle at 95° C., 1 minute, 35 cycles at 95° C. for 1 minute, 42° C. for 1 minute and 72° C. for 1 minute, 1 cycle at 72° C. for 5 minutes, and cooling to 5° C.

There were two major products of the amplification reaction: a predominant product of approximately 700 bp and a less abundant product of approximately 500 bp. The 700 bp band was isolated from a 1% "SEAPLAQUE" agarose gel using β-agarase (New England Biolabs, Beverly, Mass.) according to the supplier's instructions. This fragment was then ligated to the vector PCRII, the TA cloning vector from Invitrogen (San Diego, Calif.), following the manufacturer's instructions.

The cDNA clones of the dru1 gene were identified by screening plasmid miniprep DNA prepared from 1.6 ml of culture using the alkaline lysis method (Ausubel, et al., 1992). The cDNA product is illustrated schematically in the bottom portion of FIG. 11A, where SEQ ID NO:25 corresponds to a portion of the 3' end which includes the polyA tail. The double-stranded DNA was sequenced by the dideoxy chain-termination method using the "SEQUENASE" ver.2 enzyme and kit components (United States Biochemical, Cleveland, Ohio) and [α-$^{35}$S]-dATP (DuPont/NEN). The reactions were primed with the M13 universal forward and reverse primers (New England Biolabs, Beverly, MA). Sequencing reactions were resolved on an acrylamide gel ("LONG RANGER GEL," FMC, Rockland, Maine) and bands detected by autoradiography.

The sequence was read from the autoradiograph and analyzed for its homology with the reverse translated N-terminal protein sequence from drupel. The actual DNA sequence was determined, as opposed to the degenerate DNA sequence obtained through reverse translation of the protein sequence. The correlation between the CDNA and the remainder of the N-terminal protein sequence was confirmed. A clone (designated pAG-301) was selected, following these criteria, for further characterization. The nucleic acid sequence of the dru1 cDNA insert of pAG-301 is presented as SEQ ID NO: 16.

The entire dru1 cloning procedure from cDNA synthesis to inverse PCR of a genomic copy of the gene is shown schematically in FIGS. 11A and 11B.

EXAMPLE 4

Recovering the Genomic DNA Fragment Corresponding to the dru1 cDNA

The "CTAB" (hexadecyl-trimethyl-ammonium bromide) method (Doyle and Doyle, 1990) was used to extract DNA from raspberry leaves. PCR primers (DruGen5', SEQ ID NO:17; DruGen3', SEQ ID NO:18) were designed based upon the complete dru1 cDNA sequence. "OLIGO," a multifunctional program from National Biosciences, Inc. (Plymouth, MN), was used to facilitate design of the primers. PCR was performed following the manufacturer's procedure using "AMPLITAQ" (Perkin-Elmer Cetus), PCR buffer (50.0 mM KCl, 10 mM Tris-HCl pH 8.3, and 1.5 mM $MgCl_2$), 0.2 mM of each dNTP, raspberry genomic DNA and DruGen5' and DruGen3' primers under the following ("HOT START") conditions:

1 cycle of 97° C. for 5 minutes, after which the "AMPLITAQ" was added, 2 cycles of 97° C. for 1 minute, 52° C. for 1 minute and 720° C. for 1 minute, 25 cycles of 94° C. for 1 minute, 52° C. for 1 minute and 72° C. for 1 minute, 1 cycle of 72° C. for 5 minutes, and cooling to 5° C.

This amplification reaction produced 3 major products: a predominant product of 710 bp and 2 less abundant products of 690 and 625 bp. The PCR reaction products were then ligated to the vector PCRII, the TA 20 cloning vector from Invitrogen (San Diego, CA), following the manufacturer's instructions. A clone was selected with a 710 bp insert and designated pAG-302.

Plasmid DNA of pAG-302 was prepared from 1.6 ml of culture using the alkaline lysis method (Ausubel, et al., 1992) and sequenced by the dideoxy chain—termination method using "SEQUENASE" ver.2 enzyme and kit components (USB, Cleveland, Ohio) and [α-35S]-dATP (DuPont/NEN). The sequencing reactions were primed with the M13 universal forward and reverse primers (New England Biolabs, Beverly, Mass.). Further sequencing reactions were primed with 2 additional internal primers. Sequencing reactions were resolved on an acrylamide gel and detected through autoradiography.

The sequence of the dru1 genomic DNA insert in pAG-302 is presented as SEQ ID NO:19.

The sequence of the clone demonstrated that a genomic DNA fragment corresponding to the dru1 CDNA had been isolated.

EXAMPLE 5

Recovering the 5' Flanking Region of the dru1 Genomic DNA Through Inverse PCR Inverse PCR primers (designated DruInvUp, SEQ ID NO:5, and DruInvLow, SEQ ID NO:6) were designed based upon the genomic DNA sequence and optimized using OLIGO. Genomic raspberry DNA was digested with restriction enzyme NsiI. NsiI was chosen because, based on the cDNA sequence, NsiI was known to cut in the 3'-untranslated region of the gene. A small portion of the NsiI digested DNA was run on an analytical agarose gel and a Southern transfer was performed (Ausubel, et al., 1992).

The Southern blot was probed with the cDNA fragment contained in pAG-302. The probe identified a NsiI fragment of about 2–2.3 kb: this fragment hybridized strongly with the genomic clone. A second, smaller fragment hybridized to the probe as well but hybridized weakly with the genomic clone.

The remaining NsiI-digested raspberry DNA was electrophoresed on a 1% "SEAPLAQUE" agarose gel (FMC, Rockland, Me.). Using a BstEII lambda size standard as a guide, the digested DNA in the range of 2–2.3 kb was excised from the gel. The DNA was purified using β-agarase (New England Biolabs, Beverly, Mass.) following the manufacturer's instructions. The DNA was self ligated at a relatively dilute concentration (1 μg/ml) to bias the formation of circular ligation reaction products (Ochman, et al., 1990).

Inverse PCR was subsequently performed on the self-ligated, NsiI-digested, size-selected, genomic raspberry DNA. "AMPLITAQ" from Perkin Elmer Corporation/Applied Biosystems Division (Foster City, Calif.) was used to amplify the DNA. The manufacturer's procedure was followed using PCR buffer, 0.2 mM of each dNTP, raspberry genomic DNA (prepared as described herein), and DruInvUp (SEQ ID NO:5) and DruInvLow primers (SEQ ID NO:6). The following ("HOT START") reaction conditions were employed:

One cycle at 97° C. for 5 minutes, after which the "AMPLITAQ" was added, 2 cycles at 97° C. for 1 minute, 58° C. for 1 minute and 72° C. for 1 minute, 25 cycles at 94° C. for 1 minute, 58° C. for 1 minute and 72° C. for 1 minute, 1 cycle at 72° C. for 5 minutes, and cooling to 5° C.

This reaction produced 2 major amplification prod ucts, one of 1.8 kb and one of 900 bp. The 1.8 kb band was isolated from a 1% "SEAPLAQUE" agarose gel using β-agarase. This fragment was ligated to PCRII to give rise to pAG-310. A schematic representation of the preparation of subclone pAG-310 is presented in FIGS. 1 and 2.

The pAG-310 insert was sequenced in its entirety (SEQ ID NO:1) and the dru1 insert sequence was found to be identical to the cDNA clone (SEQ ID NO:16) and the genomic clone (SEQ ID NO:19) in the regions where sequence was shared. The normal elements of plant genes and their regulatory components were identified (FIGS. 6A and 6B) including a CAAT box, TATA box, ATG start codon, two exons, an intron, splicing sites, a stop codon and poly-adenylation sites.

Figure 12:
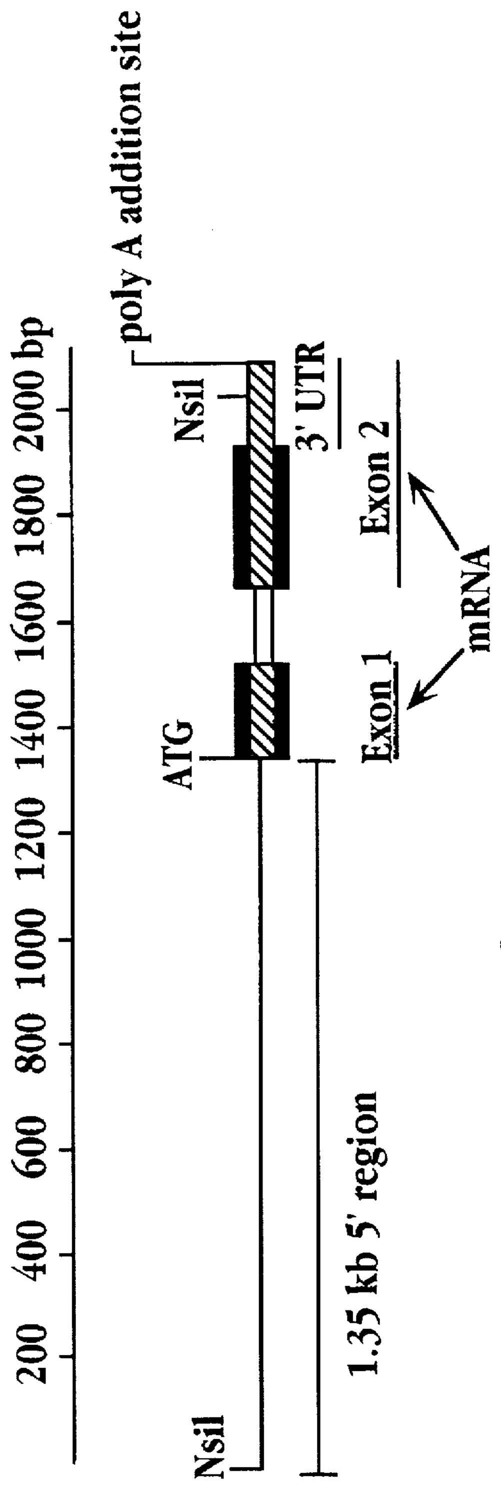
FIG. 12 presents a schematic representation of the gene organization and protein structure of dru1.
Figure 13:
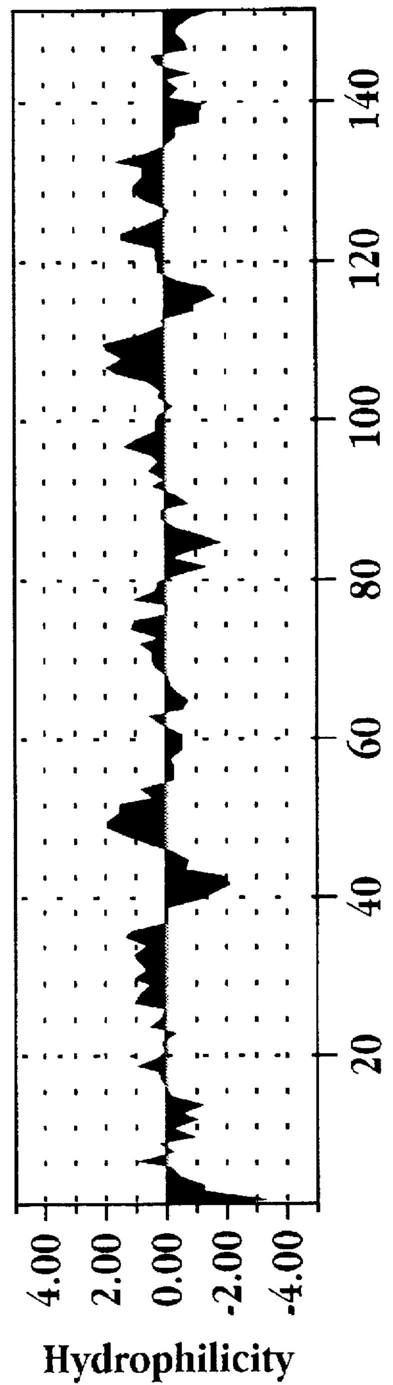
FIG. 13 presents a Kyte-Doolittle hydrophilicity plot of the coding sequence of dru1. In the figure, the hydrophilicity window size=7.

The gene organization and protein structure of dru1 is schematically displayed in FIG. 12. The gene encodes a protein having the predicted amino acid sequence presented as SEQ ID NO:20. The predicted protein has a calculated molecular weight of 17,087.64 and an estimated pI of 4.80. A Kyte-Doolittle hydrophobicity plot of the dru1 protein is presented as FIG. 13.

EXAMPLE 6

Characterization of dru1 Gene Expression

A. RNA Dot Blots

RNA dot blots were prepared using 5 μg of total raspberry leaf RNA and 5 μg each of total receptacle RNA from green, mature green, breaker, and orange/ripe raspberries (corresponding to stages I, II, III, IV, respectively, in FIG. 14). The blots were probed with the dru1 cDNA fragment, labeled with [32-P]dCTP (>3000 Ci/mmole) by the random primed method (Boeringer Mannheim Biochemicals, Random Primed reaction kit, Indianapolis, Ind.).

The blots were allowed to hybridize overnight at 45° C. in "HYBRISOL I" (Oncor, Gaithersburg, Md.). A probe concentration of $1.2 \times 10^7$ DPM/ml was used. The blot was washed after the overnight hybridization with a final wash using 0.1×SSC at 42° C. for 1 hour. The hybridizing probe was detected through standard autoradiographic methods. The exposure of the blot to film was for 4 hours and 10 minutes with an intensifying screen at −80° C.

The results of this analysis are shown in FIG. 14. In the figure the RNA dots are, respectively from left to right, leaf RNA and receptacle RNA from green (FIG. 14, "I"), mature green (FIG. 14, "II"), breaker (FIG. 14, "III") and orange/ripe raspberries (FIG. 14, "IV").

B. Further RNA Hybridization Analysis

A plant RNA extraction method (chang, et al., 1993) was used for receptacles and leaves. The raspberry drupelet RNA extraction method described above was used for the drupelets and strawberry fruit.

A Northern blot was prepared using 5 μg/lane of each sample RNA. The RNA samples were as follows: raspberry leaf (FIG. 15, lane 1), mature green raspberry receptacles (FIG. 15, lane 2), orange/ripe raspberry receptacles (FIG. 15, lane 3), mature green raspberry drupelets (FIG. 15, lane 4), and orange/ripe raspberry drupelets (FIG. 15, lane 5).

The blot was probed with the dru1 cDNA fragment, labeled with [$^{32}$P]dCTP (>3000 Ci/mmole) by random primed reactions. Hybridization was carried out overnight at 45° C. in "HYBRISOL I" (Oncor, Gaithersburg, Md.). A probe concentration of $4.2 \times 10^6$ DPM/ml was used. The blot was washed after the overnight hybridization with The hybridizing probe was detected through standard autoradiographic methods. The exposure of the blot to film was for 1 hour at room temperature without an intensifying screen.

The results of this analysis are presented in FIG. 15 and support a stage specific expression pattern in drupelets.

C. Protein Expression Analysis

Protein lysates were prepared (as described in Example 1) from raspberry drupelets at various stages of ripening. The lysates were size-fractionated by PAGE and the gel stained with Coomaise blue (50% MeOH, 10 mM Tris-HCl pH 8.3, 1.5 mM MgCl2). The results are presented in FIG. 16. In the figure the lysates in the lanes were as follows: lane 1, green drupelet; lane 2, mature green drupelet; lane 3, breaker drupelet; lane 4, orange drupelet; and lane 5, ripe drupelet. The results of this analysis supports a stage specific expression pattern in drupelets.

EXAMPLE 7

Creation of Subclone pAG-431 Containing the dru259 Promoter

Creation of subclone pAG-310 containing the fulllength dru1 promoter is described in Example 5 above.

A DNA fragment containing the dru1 promoter was PCR amplified from subclone pAG-310 using primers, 5' primer, Drupeup (SEQ ID NO:7) and 3' primer, DrupeLow (SEQ ID NO:8) under standard PCR reaction conditions.

The PCR reaction mixture contained the following components: 79.0 μl water, 10.0 μl 10×Vent buffer, 1.0 μl DrupeUp primer (50 μM solution), 1.0 μl DrupeLow primer (50 μM solution), 8.0 μl dNPTs (2.5 mM each), 1.0 μl template DNA (100 ng). The PCR reaction conditions employed were as follows:

1 cycle at 97° C., 4 minutes, after which AMPLITAQ was added;

25 cycles at 94° C. for 1 minute, 49° C. for 1 minute, and 72° C. for 1 minute, 1 cycle at 72° C. for 5 minutes, followed by cooling to 5° C.

The amplification reaction produced a 1.3 kb fragment product as illustrated in the top portion of FIGS. 1 and 2.

This fragment was purified from the reaction mixture as follows. The PCR reaction mixture was transferred to a light Phase Lock Gel tube (5 Prime to 3 Prime, Boulder, Colo.). The following solvent combination, phenol:chloroform:isoamyl alcohol (25:24:1), was added to this tube at a volume equal to the PCR reaction volume. The tube was spun in a microcentrifuge following the manufacturer's instructions. The upper aqueous phase was transferred to a Select, G-50 spin column (5 Prime to 3 Prime, Boulder, Colo.) and the DNA was centrifuged through the column according to the manufacturer's instructions. To the eluant was added 1/10 volume of 3M sodium acetate and 2.5 volumes of ethanol, in order to precipitate the DNA. The sample was incubated on ice for a period of no less than 10 minutes, and then microcentrifuged at 4° C. for 30 minutes at 14,000 rpm. The supernatant was decanted from the tube and the pellet washed twice with 75% ethanol. The pellet was allowed to dry, and then resuspended in 25 μl ½ strength TE (5 mM $Tris.HCl_1$, 0.5 mM EDTA, pH 8). The DNA fragment was digested to completion with restriction enzymes NsiI and XbaI to produce a dru1 promoter fragment. This fragment was purified in the same manner as was the PCR product described above.

The non-integrating plant expression vector p35S-GFP (Clontech Laboratories, Palo Alto, CA) was digested with XbaI and PstI. The digested plasmid was run on a 1% low melting point agarose gel (SeaPlaque, FMC BioProducts, Rockland, Me.). The gel region containing the 3.7 kb fragment was cut from the body of the gel. The DNA fragment was then purified away from the gel using β-agarase (New England Biolabs, Beverly, Mass.), following the manufacturer's instructions. The gel region containing the 0.85 kb 35S promoter was discarded. The 3.7 kb fragment from p35S-GFP2 and the 1.3 kb dru1 promoter fragment were combined in a ligation reaction, using Gibco/BRL's T4 DNA ligase, following the manufacturer's instructions, to form the intermediate plasmid pAG-155. The resulting plasmid containing the raspberry dru1 promoter was designated pAG-155, as illustrated in FIGS. 1 and 2.

Plasmid pAG-155 was digested to completion with SnaBI and EcoRV, both blunt cutters, releasing the 259 bp dru1 promoter fragment, designated herein as dru259, where nucleotide number one is immediately 5' of the ATG start codon.The digested plasmid was run on a 1% low melting point agarose gel (SEAPLAQUE, FMC BioProducts, Rockland, Me.). The gel region containing the 259 bp dru1 promoter fragment was cut from the body of the gel. The DNA fragment was then purified away from the gel using β-agarase from NEB, following the manufacturer's instructions. The gel region containing the remainder of the plasmid was discarded.

Subclone pAG-411 containing the nos::nptII cassette was prepared as follows. Cloning vector pGEM®3Zf(+) (Promega, Madison, Wis.) was digested with XbaI and BamHI. The digested plasmid was run on a 1% low melting point agarose gel ("SEAPLAQUE", FMC BioProducts, Rockland, Me.). The gel region containing the 3.2 kb fragment was cut from the body of the gel. The DNA fragment was then purified away from the gel using β-agarase (New England Biolabs, Beverly, Mailf.), following the manufacturer's instructions.

The plant binary transformation vector pGPTV-kan (Max-Planck Institut, Köln, Germany) was digested with XbaI and BamHI. The digested plasmid was run on a 1% low melting point agarose gel ("SEAPLAQUE", FMC BioProducts, Rockland, Me.). The gel region containing the 1.48 kb nos::nptII fragment was cut from the body of the gel. The DNA fragment was then purified away from the gel using β-agarase (New England Biolabs, Beverly, Mailf.), following the manufacturer's instructions. The gel region containing the 13.3 kb fragment was discarded.

The 3.2 kb fragment from pGEM®03Zf(+) and the 1.48 kb nos::nptII fragment were combined in a ligation reaction, using Gibco/BRL's T4 DNA ligase, following manufacturer's instructions to form the intermediate plasmid pAG-411.

Plasmid pAG-411 was digested to completion with HincII and PshAI, both blunt cutters, releasing the 636 bp nos promoter fragment. The digested plasmid was run on a 1% low melting point agarose gel ("SEAPLAQUE", FMC BioProducts, Rockland, Me.). The gel region containing the 4 kb fragment was cut from the body of the gel. The DNA fragment was then purified away from the gel using β-agarase (New England Biolabs, Beverly, Mailf.), following the manufacturer's instructions. The gel region containing the 636 bp nos promoter fragment was discarded.

The 4 kb fragment from pAG-411 and the 259 bp dru1 promoter fragment from pAG-155 were combined in a ligation reaction, using Gibco/BRL's T4 DNA ligase, following manufacturer's instructions, to form the intermediate vector pAG-431. The nucleotide sequence for the truncated promoter dru259 is presented herein as SEQ ID NO:4.

EXAMPLE 8

Creation of Subclone pAG-421 Containing the dru1 lo Promoter

Construction of plasmid pAG-155, containing the full-length dru1 promoter is described in Example 7.

A DNA fragment containing 166 bp of the dru1 promoter was PCR amplified from subclone pAG-155 using primers Dru1-118H3 (SEQ ID NO:9) and GFPStartR (SEQ ID NO:10) under the following PCR reaction conditions.

- One cycle at 97° C. for 3 minutes, after which the AMPLITAQ was added;
- Two cycles at 97° C. for 1 minute, 47° C. for 1 minute and 72° C. for 1 minute;
- 25 cycles at 94° C. for 1 minute, 47° C. for 1 minute and 72° C. for 1 minute;
- One cycle at 72° C. for 5 minutes, followed by cooling to 5° C.

The 166 bp of the dru1 promoter fragment was then purified as follows. The PCR reaction mixture was transferred to a light Phase Lock Gel tube (5 Prime to 3 Prime, Boulder, Colo.). A mixed solvent system containing phenol:chloroform:isoamyl alcohol (25:24:1) was added to this tube at a volume equal to the PCR reaction volume. The tube was then spun in a microcentrifuge following the manufacturer's instructions. The upper, aqueous phase was transferred to a Select, G-50 spin column (5 Prime to 3 Prime, Boulder, Colo.) and the was DNA centrifuged through the column following the manufacturer's instructions. To the eluant 1/10 volume of 3M sodium acetate and 2.5 volumes of ethanol were added, to precipitate the DNA. The sample was incubated on ice for a period of no less than 10 minutes. Following incubation, the sample was microcentrifuged at 4° C. for 30 minutes at 14,000 rpm. The supernatant was decanted from the tube and the pellet washed twice with 75% ethanol. The pellet was allowed to dry, followed by resuspension in 31.6 μl $H_20$. This fragment was digested to completion with restriction enzymes HindIII and EcoRV to produce a 112 bp dru1 promoter fragment. This fragment was purified in the same manner as the PCR product described above.

Creation of subclone pAG-411 containing the nos::nptII cassette is described in Example 7 above.

Plasmid pAG-411 was digested to completion with HindIII and PshAI, releasing a 620 bp nos promoter fragment. The digested plasmid was run on a 1% low melting point agarose gel ("SEAPLAQUE", FMC BioProducts, Rockland, Me.). The gel region containing the 4 kb fragment was cut from the body of the gel. The DNA fragment was then purified away from the gel using β-agarase (New England Biolabs, Beverly, Mass.), following the manufacturer's instructions. The gel region containing the 420 bp nos promoter fragment was discarded.

The 4 kb fragment from pAG-411 and the 112 bp dru1 promoter fragment derived from pAG-155 were combined in a ligation reaction, using Gibco/BRL's T4 DNA ligase, following manufacturer's instructions to form the intermediate vector pAG-421. The steps followed in constructing plasmid pAG-421 are represented schematically in FIG. 2.

EXAMPLE 9

Construction of a Binary Plant Transformation Vector pAG-7342 Containing a dru259::nptII Chimeric Gene A. Construction of Plasmid pAG-1542

A flow chart summarizing the construction of plasmid pAG-1542 is illustrated in FIG. 17. Plasmid pAG-1542 was constructed using conventional cloning techniques known in the art (Sambrook, et al., 1989). Subcloning binary vector pAG-1542 contained the nptII marker gene under the control of the nos promoter located near the left border and the SAMase gene (Ferro, et al., 1995) driven by the tomato E8 promoter (Deikman, et al., 1988; Deikman, et al., 1992) located near the right border.

B. Construction of Binary Plant Transformation Vector, pAG-7342

Construction of subclone pAG-431, containing the dru259::nptII chimeric gene, is described in Example 7.

Plasmid pAG-1542 was digested with HindIII and BamHI. The digested plasmid was run on a 1% low melting point agarose gel ("SEAPLAQUE", FMC BioProducts, Rockland, ME). The gel region containing the 13 kb fragment was cut from the body of the gel. The DNA fragment was then purified away from the gel using β-agarase (New England Biolabs, Beverly, Mass.), following the manufacturer's instructions. The gel region containing the 1.46 kb nos::nptII fragment was discarded.

Plasmid pAG-431 was digested with HindIII and BamHI. The digested plasmid was run on a 1% low melting point agarose gel ("SEAPLAQUE", FMC BioProducts, Rockland, Me.). The gel region containing the 1.1 kb dru259::nptII fragment was cut from the body of the gel. The DNA fragment was then purified away from the gel using β-agarase (New England Biolabs, Beverly, Mass.), following the manufacturer's instructions. The gel region containing the remainder of the plasmid was discarded.

The 13 kb fragment from pAG-1542 and the 1.1 kb dru259::nptII fragment from pAG-431 were combined in a ligation reaction, using Gibco/BRL's T4 DNA ligase, following manufacturer's instructions to form the binary plant transformation vector pAG-7342.

Construction of binary plant transformation vector pAG-7342 is depicted schematically in FIG. 4.

EXAMPLE 10

Construction of a Binary Plant Transformation Vector Containing a dru110::nptII Chimeric Gene Construction of plasmid pAG-1542 is described in Example 9A.

Construction of subclone pAG-421, containing the dru110::nptII chimeric gene, is described in Example 8.

Plasmid pAG-1542 was digested with HindIII and BamHI. The digested plasmid was run on a 1% low melting point agarose gel ("SEAPLAQUE", FMC BioProducts, Rockland, Me.). The gel region containing the 13 kb fragment was cut from the body of the gel. The DNA fragment was then purified away from the gel using β-agarase (New England Biolabs, Beverly, Mass.), following the manufacturer's instructions. The gel region containing the 1.46 kb nos::nptII fragment was discarded. Plasmid pAG-421 was digested with HindIII and BamHI. The digested plasmid was run on a 1% low melting point agarose gel ("SEAPLAQUE", FMC BioProducts, Rockland, Me.). The gel region containing the 0.95 kb dru259::nptII fragment was cut from the body of the gel. The DNA fragment was then purified away from the gel using β-agarase from New England Biolabs (Beverly, Mass.), following the manufacturer's instructions. The gel region containing the remainder of the plasmid was discarded.

The 13 kb fragment from pAG-1542 and the 0.95 kb dru110::nptII fragment from pAG-421 were combined in a ligation reaction, using Gibco/BRL's T4 DNA ligase, following manufacturer's instructions to form the binary plant transformation vector pAG-7242. Construction of binary plant transformation vector pAG-7242 is depicted schematically in FIG. 3.

EXAMPLE 11

Plant Transformation Using Binary Vectors pAG-7242 and pAG-7342

Agrobacterium-based plant transformation using binary vectors pAG-7242 and pAG-7342 containing chimeric dru110::nptII and dru254::nptII genes, respectively, was carried out using tomato cotyledons as described below for exemplary plasmid pAG-7242.

A cherry tomato line (CH3) obtained from Sunseeds Co. (Morgan Hill, CA) was used as the target for plant transformation experiments. Transformation was carried out using a standard cotyledon-based Agrobacterium cocultivation method (Fillatti, et al., 1987).

*Agrobacterium tumefaciens* strain EHA101 (Hood, et al., 1986), a disarmed derivative of *Agrobacterium tumefaciens* strain C58, was used to introduce coding sequences into plants. This strain contains a T-DNA-less Ti plasmid. The pAG-7242 plasmid was transferred into EHA101 using electroporation essentially as described by Nagel, et al. (1990). Briefly, an *Agrobacterium tumefaciens* culture was grown to mid-log phase (OD 600 0.5 to 1.0) in MG/L agar media containing tryptone (5 g/l), yeast extract (2.5 g/l), NaCl (5 g/l), mannitol (5 g/l), sodium glutamate (1.17 g/l), $K_2HPO_4$ (0.25 g/l), $MgSO_4$ (0.1 g/l) and biotin (2 μg/l), adjusted to pH 7.2 by addition of sodium hydroxide.

After cutting off from each end approximately one third of the tomato cotyledon, the middle third was used as the tissue explant. Cotyledon explants were pre-conditioned overnight on tobacco feeder plates (Fillatti, et al., 1987). The preconditioned explants were inoculated by placing them in a 20 ml overnight culture of EHA105/pAG-7242 for 15 minutes. The explants were then co-cultivated with EHA105/pAG-7242 for 2 days on tobacco feeder plates as described by Fillatti, et al., (1987).

The explants were grown in tissue culture media containing 2Z media (Fillatti, et al., 1987), Murisheegee and Skoog (MS) salts, Nitsch and Nitsch vitamins, 3% sucrose, 2 mg/l seatin, 500 mg/l carbenicillin, 60–200 mg/l kanamycin, and 0.7% agar. The explants were grown in tissue culture for 8 to 10 weeks. The carbenicillin treatments were kept in place for 2 to 3 months in all media. The explants and plants were kept on carbenicillin until they were potted in soil as a counter-selection to rid the plants of viable *Agrobacterium tumefaciens* cells.

Table 1 presents a summary of the plant transformation experiments, including concentrations of selection agent utilized, and transformation frequencies. Results obtained for plant transformation experiments using the novel raspberry promoters of the present invention are compared to those obtained using binary vectors containing two different strong constitutive promoters, a caulimovirus promoter, the cassava mottle vein virus promoter (CAS) and the hsp80 promoter. The CAS promoter was obtained from The Scripps Research Institute (La Jolla, Calif). Isolation of the hsp80 promoter, its nucleotide sequence, as well as vector constructions and expression levels of transgenes containing the hsp80 promoter have been described (Brunke and Wilson, 1993).

A comparison of the relative strength of nptII expression across 10 transgenic events from transformants produced using four of the promoter-nptII chimeric gene combinations described above is presented in FIG. 5.

EXAMPLE 12

Relative Expression of the nptII Marker Gene in Transgenic Plants Containing Promoters Derived From Raspberry Leaf tissues from 10 separate transgenic events employing vectors pAG7242 and pAG-7342, containing raspberry promoters dru110 and dru254, respectively, were assayed by ELISA to determine nptII expression levels, according to the manufacturer's (5'-3', Inc., Boulder, Colo.) recommended protocols for (i) protein extraction and (ii) determination of nptII expression levels. Results from the transformation experiments are provided in Tables 1 and 2 below.

The nptII assay was carried out with a few samples using rooted plants which were available in culture at the time of testing. Thus, not all rooted plants were tested for nptII expression. The results of the ELISA assay are presented in column (IV) of Table 1 below.

TABLE 1

Transformation Results

| (I) Promoter | (II) Selection Conc. of kanamycin (mg/l) | (III) Transformation Frequency | (IV) nptII Expression |
|---|---|---|---|
| CAS | 200 | 50% | 100% (10/10) |
| dru259 | 90 | 60% | 67% (4/6) |
| | 200 | 55% | 75% (3/4) |
| dru110 | 60 | 63% | 17% (1/6) |
| | 90 | 47% | 67% (2/3) |
| | 200 | 30% | 100% (1/1) |
| hsp80 | 60 | 50% | 63% (5/8) |
| | 90 | 27% | 100% (1/1) |
| | 200 | 60% | 100% (1/1) |

In referring to the data presented in Table 1, transformation frequency is defined as the ratio of the number of tissue explants producing regenerated shoots that are capable of rooting in the presence of selection agent (kanamycin) to the total number of initial tissue explants, expressed as a percentage. NptII expression level, expressed as a percentage, is the ratio of nptII positive plants to the total number of rooted plants tested for nptII, based upon the results of the ELISA assay described in Example 12. A positive nptII result is an ELISA value greater than background. For example, the first entry under column (IV) indicates that out of 10 events tested for nptII, 10 exhibited positive ELISA results.

Relative expression levels of nptII are presented in Table 2. The data from transgenic plants containing the CAS::nptII construct are not included in Table 2 due to the high expression levels observed in transformants containing the CAS promoter. Values from the two CAS::nptII events assayed were in excess of 6000 pg/ml of nptII.

Figure 5:
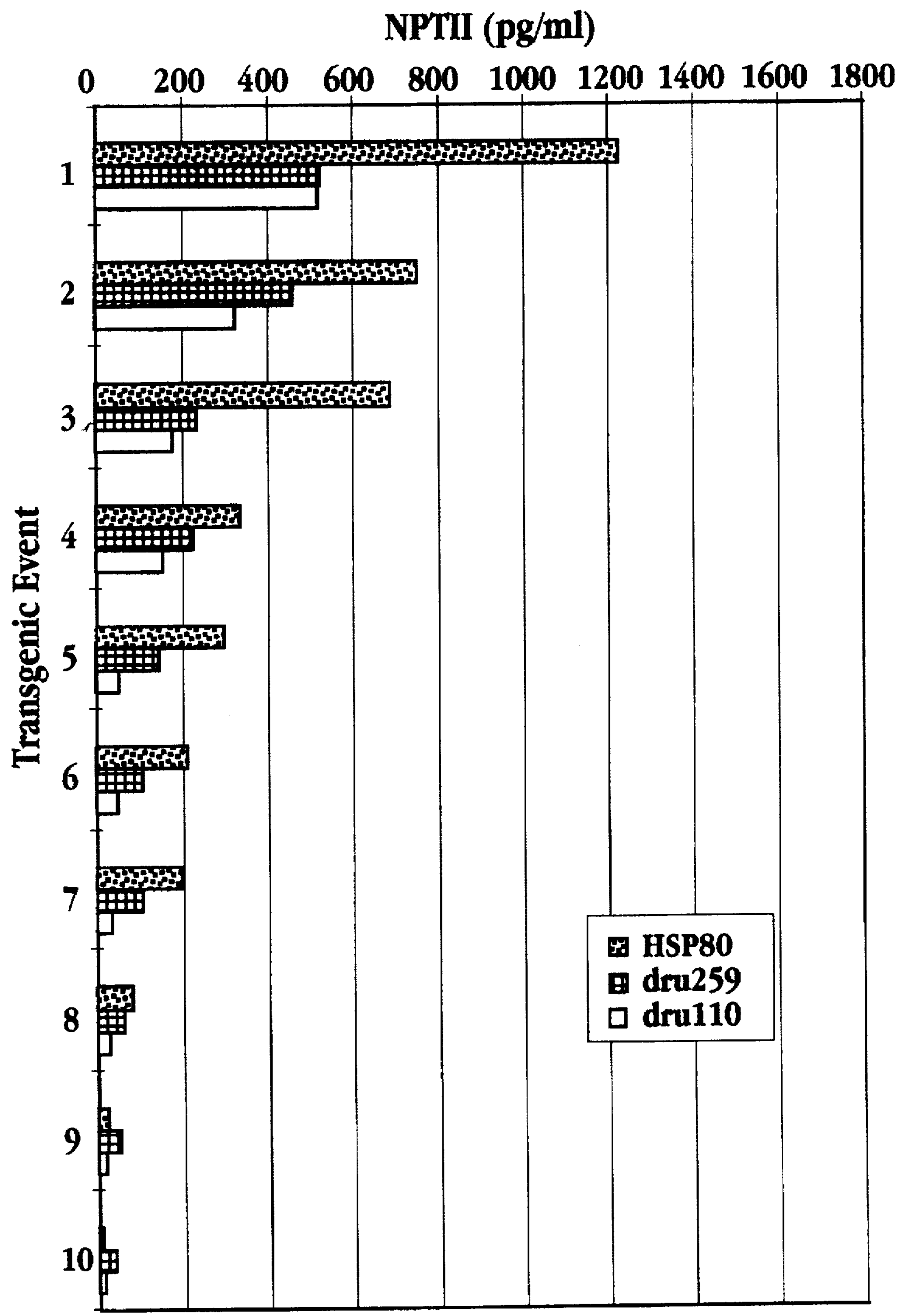
FIG. 5 is a graph representing relative levels of nptII gene expression across 10 transgenic events for three different promoter-nptII chimeric gene combinations.

The range of expression across events presented in Table 2 below as well as illustrated graphically in FIG. 5 is typical for transgene expression in plants.

TABLE 2

Expression of nptII (pg/ml)

| Transgenic Event | hsp80 | dru259 | dru110 |
|---|---|---|---|
| 1 | 1223 | 523.66 | 518.1 |
| 2 | 748.7 | 454.84 | 324.6 |
| 3 | 687.3 | 231.64 | 174 |
| 4 | 332.1 | 222.34 | 151.7 |
| 5 | 294.9 | 144.22 | 51.22 |
| 6 | 207.5 | 107.02 | 49.36 |
| 7 | 194.4 | 103.3 | 34.48 |
| 8 | 79.12 | 64.24 | 30.76 |
| 9 | 21.46 | 51.22 | 17.74 |
| 10 | 10.3 | 38.2 | 12.16 |

The data above indicate that the exemplary dru259 and dru1 lo promoters direct lower level expression of genes placed under their control than does the hsp80 promoter. However, these two exemplary raspberry dru promoters are both capable of expressing sufficient levels of nptII to allow selection of transgenic plants.

While the invention has been described with reference to specific methods and embodiments, it will be appreciated that various modifications and changes may be made without departing from the invention.

It is claimed:

1. A chimeric gene which is expressed in plant cells, comprising:

(i) a raspberry dru1 promoter, and (ii) a DNA sequence encoding a product of interest, where said DNA sequence is heterologous to said promoter and said DNA sequence is operably linked to said promoter to enable constitutive expression of said product.

2. A chimeric gene of claim 1, where said DNA sequence encodes a polypeptide which confers herbicide-resistance to transformed plant cells expressing said polypeptide.

3. A chimeric gene of claim 1, wherein the nucleotide sequence of the promoter is contained in the sequence presented as SEQ ID NO:1.

4. A chimeric gene of claim 1, wherein said heterologous DNA sequence comprises an nptII gene.

5. A chimeric gene of claim 1, where said DNA sequence encodes a polypeptide that permits selection of transformed plant cells containing said gene by rendering said cells resistant to an amount of an antibiotic that is toxic to non-transformed plant cells.

6. A chimeric gene of claim 5, wherein said polypeptide is selected from the group consisting of neomycin phosphotransferase, hygromycin phosphotransferase, and bromoxynil-specific nitrilase.

7. A plant transformation vector containing the chimeric gene of claim 5.

8. A kit for providing expression of a selectable marker gene in transgenic plants, comprising the vector of claim 7.

9. A chimeric gene of claim 1, wherein the promoter is the dru110 or the dru259 promoter.

10. A plant transformation vector containing the chimeric gene of claim 9.

11. A chimeric gene of claim 1, wherein the nucleotide sequence of said promoter consists of SEQ ID NO:3.

12. A plant transformation vector containing the chimeric gene of claim 11.

13. A chimeric gene of claim 1, wherein the nucleotide sequence of said promoter consists of SEQ ID NO:4.

14. A plant transformation vector containing the chimeric gene of claim 11.

15. A plant transformation vector containing the chimeric gene of claim 1.

16. A kit for transforming plants, comprising the plant transformation vector of claim 15.

17. A method for producing a transgenic plant, comprising:

transforming progenitor cells of a plant with the chimeric gene of claim 1 to produce transformed progenitor cells, and growing the transformed progenitor cells to produce a transgenic plant.

18. The method of claim 17, wherein the chimeric gene in said transforming step is the chimeric gene of claim 7.

19. A method for providing expression of a selectable marker gene in transgenic plants, comprising:

(i) transforming progenitor cells of a plant with the chimeric gene of claim 1, wherein said DNA sequence comprises a selectable marker gene functional in plant cells, where expression of said product confers to plant cells containing said gene the ability to grow in the presence of a selective agent, (ii) selecting plant cells which have been transformed by their ability to grow in the presence of an amount of selective agent that is toxic to non-transformed plant cells, (iii) regenerating said transformed plant cells to provide a differentiated plant, and (iv) selecting a transformed plant which expresses said product.

20. A method of claim 19, where said transforming comprises transforming progenitor cells of the plant with a vector containing said chimeric gene.

21. The method of claim 19, where said selective agent is selected from the group consisting of hygromycin, geneticin, and kanamycin.

22. The method of claim 19, where said selectable marker gene is selected from the group consisting of a neomycin phosphotransferase (npt) gene, a hygromycin phosphotransferase (hpt) gene, and a bromoxynil-specific nitrilase (bxn) gene.

23. The method of claim 19, wherein said promoter is the dru110 or the dru259 promoter.

24. A plant cell comprising a chimeric gene of claim 1.

25. A plant cell of claim 24, wherein said DNA sequence encodes a polypeptide that permits selection of transformed plant cells containing said gene by rendering said cells resistant to an amount of an antibiotic that is toxic to non-transformed plant cells.

26. A plant cell of claim 24, in which the promoter is the dru110 or the dru259 promoter.

27. A transgenic plant containing a chimeric gene comprising:

(i) a raspberry dru1 promoter, and (ii) a DNA sequence encoding a product of interest, where said DNA sequence is heterologous to said promoter and said DNA sequence is operably linked to said promoter to enable constitutive expression of said product.

28. The plant of claim 27, wherein said promoter is the dru110 or the dru259 promoter.

29. An isolated DNA molecule comprising a constitutive raspberry promoter from a raspberry dru1 gene.

30. The DNA molecule of claim 29, wherein the promoter is the dru110 or the dru259 promoter.

31. A DNA construct comprising:

(i) a raspberry dru1 promoter, and (ii) a DNA sequence encoding a product of interest, where said DNA sequence is heterologous to said promoter and said DNA sequence is under the regulatory control of said promoter to enable constitutive expression of said product.

32. The DNA construct of claim 31, wherein the raspberry promoter is the dru110 or the dru259 promoter.

33. A kit for providing expression of a selectable marker gene in transgenic plants, comprising a plant transformation vector containing a chimeric gene composed of (i) a raspberry dru1 promoter, and, operably linked to said promoter, (ii) a heterologous DNA sequence encoding neomycin phosphotransferase.

34. The kit of claim 33, wherein the raspberry promoter is the dru110 or the dru259 promoter.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 2213 base pairs
( B ) TYPE: nucleic acid
( C ) STRANDEDNESS: both
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: pAG310 insert sequence (dru 1 gene)

( x i ) SEQUENCE DESCRIPTION: SEQ ID NO:1:

```
ATGCATATCA ACAACTACGA ATAAAGAGAT CAGCCTTTCC GTATCTGGTG GATGTTTGAG    60

TCGGTGATGA CCATCTAATT AAAGAAAGAA GAAAAATTAT ACATATTGTG GACCTCCCCA   120

TATATAATTC TTATCATCTT TGTTACTGCC ATTATGATTA TAAAATGATA TTAAAGGGAT   180

GGTGTACCGT GTACTAATCA AATATCTACC TGATCTTATT GATTTGAAAG ATCATAAAAA   240

GAAATTAAAA TTGTTCAAAA TAAACCCCTA GAATTATATA TAGTTCATTA AGTTCAAATT   300

AATTCGTTTG AAACGTGTTA AGCAACCCTA CAACGTACTA AGCACCCTAG CTCCCTTTGC   360
```

CTCTCGGCGG TAAGAGGAGA TATCCTCAGT CGAATTATGA GCCGATCGAG GAAAGCTCGA 420

TCAGTTGGAA AATCTTTCTT TCTTATGGCC AAGTTGTTTC AAACAATATA TTGAATTATT 480

GACTCTTAGC AACTTAAGTT TCAAACCGTG ACGAACCAAT AAAATTTGAC AAATTAATCA 540

CTTTAAGTGC CTAGTGGATC AGCGTCTAGG TTGGGAACCC CTCTACCTGC GTTTGATTCA 600

CCAAGCTATC AAAATGGTCA GACACTGTGC TGCAATGCAC AATTGGAGCA TTTCACATGC 660

GTTGCATGAA TTATTCCTTG GGTTAGGAAA CCTTTGAAAT ACCTTGACTA AGGTAAAAAA 720

AAAAACTTGA CAAATTAATA AATATTAATA TTGATTTTGT ACGTACACGA CTTAACCAAA 780

CTCTCAATGA TTTATTGATT TCTAATATAT ATATTAATAA CGTACGTCTA ATTGGATCAT 840

TCATGATCTA CAGCCATCAC ATCTCAGATG ATTTTCTTGC AATGAATTGC CTAAGCTGGC 900

GTTATTATCT TTTTTCATA ATACAGTTTT AAAAAAGGGT ACGTATTGGA GCTGGTGATG 960

ACTTCTTAAG AAACAACAAA TTAACGCCAT AGCTATTTGA TTTATATATC CAAAAGGAGA 1020

AAATGTATAA GATCGTTGCT TACTTAATTT GCAGGCTAGG TTAATTGACA TCAAATAATT 1080

GAAGAGTACG TAGGGCCAAT GTTGCTGAGA TCTAGCATCA ATAATAGGAT TTGGCTTGTC 1140

GATCGATCAT CTTTATTTAA TTGAGAGGTA TGTATCCATA TGTTTTCTGA AATTAAAATA 1200

TTACCTAATA ATTGAGCTGA AACTGTAGTG AATTTAACCT TTTCTAAGTT CTGCCCATAT 1260

ATAACATACC ACATAGGTAG CTGATCGATC GATCATATAT ATGTACTTAG GGTTCTGATC 1320

AGTATCAATA TCGATCACAA GTGCTGATAA TTAAACATGG TTCTTCAAGG TAAGGTGGAG 1380

GCTGACATTG AAATCTCAGC ACCTGCTGAC AAGTTCTACA ACCTCTTCAA GAGTGAGGCT 1440

CACCACGTCC CCAAAACTTC TCAAACTGGC ACCATAACCG GAGTTGCGGT GCATGAAGGA 1500

GACTGGGAAA CTGATGGCTC CATTAAGATT TGGAATTATG CAATAGGTAA GCCATTATGT 1560

TGTTAGATTG TTAATTTAGA TTATTAACCA AAGCTGGCTT TGAATCACTA CAATATATAT 1620

TAGGGCACGC CAGTACAGAT TTTCTGTTTA TAATTGTTTC AGTGATTATT TTCTTACAAA 1680

TATAGAGGGC GAAGTGGGAA CATTCAAGGA GAAAGTAGAG CTAGACGATG TGAACAAGGC 1740

AATAATTCTG AATGGGTTGG AAGGAGATGT GTTCCAGTAT TACAAGAGCT TCAAGCCCGT 1800

CTATCAATTC ACTCAAAAGA ATGATGGCAG CAGCATTGCC AAAGTGTCCA TTGAATATGA 1860

GAAACTGAGT GAGGAAGTTG CAGATCCAAA TAAGTACATT CGCTTGATGA CTAATATCGT 1920

CAAGGATCTT GATGCCCACT TCATCAAGGC ATAAAAGGGA TATTATAATA AATCAAGCAT 1980

ATGAAACACG ATGAAAAGAG AGCTAGCCAC TATCTACTGC TGGTTTATAA GTTTAAAGAT 2040

AATCATGTGA ACGTTGTAAT GCATGCTTTG TTTGGTTACT TCGTTTTAAT GTCTTGTTAT 2100

GCACTAATAC CGTCAGTGTA ATAAAAGCTA GTGTGAAAGG ATCTGATATA TTGTGATGTA 2160

TCATGTATTC AACTACCAAC TATATATGGT ATCATATTTA TATATCAAAT AAA 2213

( 2 ) INFORMATION FOR SEQ ID NO:2:

( i ) SEQUENCE CHARACTERISTICS:
( A ) LENGTH: 1356 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Exemplary full length dru1 promoter sequence ( x i ) SEQUENCE DESCRIPTION: SEQ ID NO:2:

```
ATGCATATCA ACAACTACGA ATAAAGAGAT CAGCCTTTCC GTATCTGGTG GATGTTTGAG     60
TCGGTGATGA CCATCTAATT AAAGAAAGAA GAAAAATTAT ACATATTGTG GACCTCCCCA    120
TATATAATTC TTATCATCTT TGTTACTGCC ATTATGATTA TAAAATGATA TTAAAGGGAT    180
GGTGTACCGT GTACTAATCA AATATCTACC TGATCTTATT GATTTGAAAG ATCATAAAAA    240
GAAATTAAAA TTGTTCAAAA TAAACCCCTA GAATTATATA TAGTTCATTA AGTTCAAATT    300
AATTCGTTTG AAACGTGTTA AGCAACCCTA CAACGTACTA AGCACCCTAG CTCCCTTTGC    360
CTCTCGGCGG TAAGAGGAGA TATCCTCAGT CGAATTATGA GCCGATCGAG GAAAGCTCGA    420
TCAGTTGGAA AATCTTTCTT TCTTATGGCC AAGTTGTTTC AAACAATATA TTGAATTATT    480
GACTCTTAGC AACTTAAGTT TCAAACCGTG ACGAACCAAT AAAATTTGAC AAATTAATCA    540
CTTTAAGTGC CTAGTGGATC AGCGTCTAGG TTGGGAACCC CTCTACCTGC GTTTGATTCA    600
CCAAGCTATC AAAATGGTCA GACACTGTGC TGCAATGCAC AATTGGAGCA TTTCACATGC    660
GTTGCATGAA TTATTCCTTG GGTTAGGAAA CCTTTGAAAT ACCTTGACTA AGGTAAAAAA    720
AAAAACTTGA CAAATTAATA AATATTAATA TTGATTTTGT ACGTACACGA CTTAACCAAA    780
CTCTCAATGA TTTATTGATT TCTAATATAT ATATTAATAA CGTACGTCTA ATTGGATCAT    840
TCATGATCTA CAGCCATCAC ATCTCAGATG ATTTTCTTGC AATGAATTGC CTAAGCTGGC    900
GTTATTATCT TTTTTTCATA ATACAGTTTT AAAAAAGGGT ACGTATTGGA GCTGGTGATG    960
ACTTCTTAAG AAACAACAAA TTAACGCCAT AGCTATTTGA TTTATATATC CAAAAGGAGA   1020
AAATGTATAA GATCGTTGCT TACTTAATTT GCAGGCTAGG TTAATTGACA TCAAATAATT   1080
GAAGAGTACG TAGGGCCAAT GTTGCTGAGA TCTAGCATCA ATAATAGGAT TTGGCTTGTC   1140
GATCGATCAT CTTTATTTAA TTGAGAGGTA TGTATCCATA TGTTTTCTGA AATTAAAATA   1200
TTACCTAATA ATTGAGCTGA AACTGTAGTG AATTTAACCT TTTCTAAGTT CTGCCCATAT   1260
ATAACATACC ACATAGGTAG CTGATCGATC GATCATATAT ATGTACTTAG GGTTCTGATC   1320
AGTATCAATA TCGATCACAA GTGCTGATAA TTAAAC                             1356
```

( 2 ) INFORMATION FOR SEQ ID NO:3:

( i ) SEQUENCE CHARACTERISTICS:
( A ) LENGTH: 112 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: dru110 promoter sequence (minus 112 region from start codon)

( x i ) SEQUENCE DESCRIPTION: SEQ ID NO:3:

```
TAAGTTCTGC CCATATATAA CATACCACAT AGGTAGCTGA TCGATCGATC ATATATATGT     60
ACTTAGGGTT CTGATCAGTA TCAATATCGA TCACAAGTGC TGATAATTAA AC            112
```

( 2 ) INFORMATION FOR SEQ ID NO:4:

( i ) SEQUENCE CHARACTERISTICS:
( A ) LENGTH: 259 base pairs ( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Dru259 promoter sequence (minus 259 region from start codon)

( x i ) SEQUENCE DESCRIPTION: SEQ ID NO:4:

```
AATGTTGCTG AGATCTAGCA TCAATAATAG GATTTGGCTT GTCGATCGAT CATCTTTATT    60
TAATTGAGAG GTATGTATCC ATATGTTTTC TGAAATTAAA ATATTACCTA ATAATTGAGC   120
TGAAACTGTA GTGAATTTAA CCTTTTCTAA GTTCTGCCCA TATATAACAT ACCACATAGG   180
TAGCTGATCG ATCGATCATA TATATGTACT TAGGGTTCTG ATCAGTATCA ATATCGATCA   240
CAAGTGCTGA TAATTAAAC                                                259
```

( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: primer DruInvUp ( x i ) SEQUENCE DESCRIPTION: SEQ ID NO:5:

```
TGA ATG GGT TGG AAG GAG ATG TGT    24
```

( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: primer DruInvLow ( x i ) SEQUENCE DESCRIPTION: SEQ ID NO:6:

```
ATG GTG CCA GTT TGA GAA GTT TTG    24
```

( 2 ) INFORMATION FOR SEQ ID NO:7:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 5'primer DrupeUp ( x i ) SEQUENCE DESCRIPTION: SEQ ID NO:7:

CCC GTC TAG ATA TCA GCA CTT GT 23

( 2 ) INFORMATION FOR SEQ ID NO:8:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 3'primer, DrupeLow ( x i ) SEQUENCE DESCRIPTION: SEQ ID NO:8:

TGA ATC ACG ATG AAA AGA G 19

( 2 ) INFORMATION FOR SEQ ID NO:9:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: PCR reaction primer Dru1-118H3

( x i ) SEQUENCE DESCRIPTION: SEQ ID NO:9:

CGC AAG CTT TTC TAA GTT 18

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: PCR reaction primer, GFPStartR ( x i ) SEQUENCE DESCRIPTION: SEQ ID NO:10:

GTT CTT CTC CTT TAC TCA TCT 21

( 2 ) INFORMATION FOR SEQ ID NO:11:

( i ) SEQUENCE CHARACTERISTICS:
( A ) LENGTH: 30 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( C ) INDIVIDUAL ISOLATE: amino terminal drupe1 sequence ( x i ) SEQUENCE DESCRIPTION: SEQ ID NO:11:

```
Val Leu Gln Gly Lys Val Glu Ala Asp Ile Glu Ile Ser Ala Pro Ala
1               5                   10                  15

Ala Lys Phe Tyr Asn Leu Phe Lys Ser Glu Ala Xaa Trp Val
            20                  25                  30
```

( 2 ) INFORMATION FOR SEQ ID NO:12:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: dTRANDOM primer ( x i ) SEQUENCE DESCRIPTION: SEQ ID NO:12:

```
TAGGCTCGTA GACTCTTTTT TTTTTTTTTT                                      30
```

( 2 ) INFORMATION FOR SEQ ID NO:13:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( C ) INDIVIDUAL ISOLATE: dru1 partial amino acid sequence ( x i ) SEQUENCE DESCRIPTION: SEQ ID NO:13:

```
Gln Gly Lys Val Glu Ala Asp
1               5
```

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: reverse translated sequence of SEQ ID NO:1, 3'PCR primer ( x i ) SEQUENCE DESCRIPTION: SEQ ID NO:14:

CARGGNAARG TNGARCGNGA 20

( 2 ) INFORMATION FOR SEQ ID NO:15:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: 5'PCR primer, DrupeRAN18

( x i ) SEQUENCE DESCRIPTION: SEQ ID NO:15:

TAGGCTCGTA GACTCTTT 18

( 2 ) INFORMATION FOR SEQ ID NO:16:

( i ) SEQUENCE CHARACTERISTICS:
( A ) LENGTH: 751 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: pAG301 insert, dru1 cDNA clone ( x i ) SEQUENCE DESCRIPTION: SEQ ID NO:16:

CAGGGAAAGG TGGAGGCTGA CATTGAAATC TCAGCACCTG CTGACAAGTT CTACAACCTC 60

TTCAAGAGTG AGGCTCACCA CGTCCCCAAA ACTTCTCAAA CTGGCACCAT AACCGGAGTT 120

GCGGTGCATG AAGGAGACTG GGAAACTGAT GGCTCCATTA AGATTTGGAA TTATGCAATA 180

GAGGGCGAAG TGGGAACATT CAAGGAGAAA GTAGAGCTAG ACGATGTGAA CAAGGCAATA 240

ATTCTGAATG GGTTGGAAGG AGATGTGTTC CAGTATTACA AGAGCTTCAA GCCCGTCTAT 300

CAATTCACTC AAAAGAATGA TGGCAGCAGC ATTGCCAAAG TGTCCATTGA ATATGAGAAA 360

CTGAGTGAGG AAGTTGCAGA TCCAAATAAG TACATTCGCT TGATGACTAA TATCGTCAAG 420

GATCTTGATG CCCACTTCAT CAAGGCATAA AAGGGATATT ATAATAAATC AAGCATATGA 480

AACACGATGA AAAGAGAGCT AGCCACTATC TACTGCTGGT TTATAAGTTT AAAGATAATC 540

ATGTGAACGT TGTAATGCAT GCTTTGTTTG GTTACTTCGT TTTAATGTCT TGTTATGCAC 600

TAATACCGTC AGTGTAATAA AAGCTAGTGT GAAAGGATCT GATATATTGT GATGTATCAT 660

GTATTCAACT ACCAACTATA TATGGTATCA TATTTATATA TCAAATAAAT TAATGTGAAA 720

AAAAAAAAAA AAAAAAAGAG TCTACGAGCC T 751

( 2 ) INFORMATION FOR SEQ ID NO:17:

( i ) SEQUENCE CHARACTERISTICS:

-continued ( A ) LENGTH: 18 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DruGen 5'primer ( x i ) SEQUENCE DESCRIPTION: SEQ ID NO:17:

AAGGTGGAGG CTGACATT 18

( 2 ) INFORMATION FOR SEQ ID NO:18:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DruGen 3'primer ( x i ) SEQUENCE DESCRIPTION: SEQ ID NO:18:

CTGACGGTAT TAGTGCATAA CA 22

( 2 ) INFORMATION FOR SEQ ID NO:19:

( i ) SEQUENCE CHARACTERISTICS:
( A ) LENGTH: 745 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: pAG302, dru1 genomic clone ( x i ) SEQUENCE DESCRIPTION: SEQ ID NO:19:

```
AAGGTGGAGG CTGACATTGA AATCTCAGCA CCTGCTGACA AGTTCTACAA CCTCTTCAAG    60
AGTGAGGCTC ACCACGTCCC CAAAACTTCT CAAACTGGCA CCATAACCGG AGTTGCGGTG   120
CATGAAGGAG ACTGGGAAAC TGATGGCTCC ATTAAGATTT GGAATTATGC AATAGGTAAG   180
CCATTATGTT GTTAGATTGT TAATTTAGAT TATTAACCAA AGCTGGCTTT GAATCACTAC   240
AATATATATT AGGGCACGCC AGTACAGATT TTCTGTTTAT AATTGTTTCA GTGATTATTT   300
TCTTACAAAT ATAGAGGGCG AAGTGGGAAC ATTCAAGGAG AAAGTAGAGC TAGACGATGT   360
GAACAAGGCA ATAATTCTGA ATGGGTTGGA AGGAGATGTG TTCCAGTATT ACAAGAGCTT   420
CAAGCCCGTC TATCAATTCA CTCAAAAGAA TGATGGCAGC AGCATTGCCA AAGTGTCCAT   480
TGAATATGAG AAACTGAGTG AGGAAGTTGC AGATCCAAAT AAGTACATTC GCTTGATGAC   540
TAATATCGTC AAGGATCTTG ATGCCCACTT CATCAAGGCA TAAAAGGGAT ATTATAATAA   600
```

-continued

```
ATCAAGCATA TGAAACACGA TGAAAAGAGA GCTAGCCACT ATCTACTGCT GGTTTATAAG     660

TTTAAAGATA ATCATGTGAA CGTTGTAATG CATGCTTTGT TTGGTTACTT CGTTTTAATG     720

TCTTGTTATG CACTAATACC GTCAG                                           745
```

( 2 ) INFORMATION FOR SEQ ID NO:20:

( i ) SEQUENCE CHARACTERISTICS:
( A ) LENGTH: 152 amino acids
( B ) TYPE: amino acid
( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
( C ) INDIVIDUAL ISOLATE: predicted amino acid coding sequence of dru1

( x i ) SEQUENCE DESCRIPTION: SEQ ID NO:20:

```
Met Val Leu Gln Gly Lys Val Glu Ala Asp Ile Glu Ile Ser Ala Pro
1               5                   10                  15

Ala Asp Lys Phe Tyr Asn Leu Phe Lys Ser Glu Ala His His Val Pro
            20                  25                  30

Lys Thr Ser Gln Thr Gly Thr Ile Thr Gly Val Ala Val His Glu Gly
        35                  40                  45

Asp Trp Glu Thr Asp Gly Ser Ile Lys Ile Trp Asn Tyr Ala Ile Glu
    50                  55                  60

Gly Glu Val Gly Thr Phe Lys Glu Lys Val Glu Leu Asp Asp Val Asn
65                  70                  75                  80

Lys Ala Ile Ile Leu Asn Gly Leu Glu Gly Asp Val Phe Gln Tyr Tyr
                85                  90                  95

Lys Ser Phe Lys Pro Val Tyr Gln Phe Thr Gln Lys Asn Asp Gly Ser
            100                 105                 110

Ser Ile Ala Lys Val Ser Ile Glu Tyr Glu Lys Leu Ser Glu Glu Val
        115                 120                 125

Ala Asp Pro Asn Lys Tyr Ile Arg Leu Met Thr Asn Ile Val Lys Asp
    130                 135                 140

Leu Asp Ala His Phe Ile Lys Ala
145                 150
```

( 2 ) INFORMATION FOR SEQ ID NO:21:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: mRNA ( i i i ) HYPOTHETICAL: NO ( i v ) ANTI-SENSE: NO ( v i ) ORIGINAL SOURCE:
( C ) INDIVIDUAL ISOLATE: drupelet mRNA poly A region (Fig IIA)

( x i ) SEQUENCE DESCRIPTION: SEQ ID NO:21:

```
AAAAAAAAAA                                                            10
```

( 2 ) INFORMATION FOR SEQ ID NO:22:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: first cDNA strand (Fig IIA)

( i x ) FEATURE:
( A ) NAME/KEY: Other
( B ) LOCATION: 3, 6, 9, 12, 15, 18, 21, 23, 24
( D ) OTHER INFORMATION: /note= "where N is either G, A, T or C; where Y is either C or T; where R is either G or A"

( x i ) SEQUENCE DESCRIPTION: SEQ ID NO:22:

TCNGCYTCNA CYTTNCCYTG NARNAC 26

( 2 ) INFORMATION FOR SEQ ID NO:23:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: first round PCR (Fig IIA)

( x i ) SEQUENCE DESCRIPTION: SEQ ID NO:23:

AAAAAAAAAA GAGTCTACGA GCCTA 25

( 2 ) INFORMATION FOR SEQ ID NO:24:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: second round amplification cDNA (Fig I ( i x ) FEATURE:
( A ) NAME/KEY: Other
( B ) LOCATION: 3, 6, 9, 12, 15, 18
( D ) OTHER INFORMATION: /note= "where N is either G, A, T or C; where Y is either C or T; where R is either G or A"

( x i ) SEQUENCE DESCRIPTION: SEQ ID NO:24:

TCNGCYTCNA CYTTNCCYTG 20

( 2 ) INFORMATION FOR SEQ ID NO:25:

-continued ( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( C ) INDIVIDUAL ISOLATE: amplified dru1 cDNA (Fig 11A)

( x i ) SEQUENCE DESCRIPTION: SEQ ID NO:25:

AAAAAAAAAA AAAAAAAAAA GAGTCTACGA GCCTA 35